(12) United States Patent
Gibson et al.

(10) Patent No.: US 7,322,965 B2
(45) Date of Patent: Jan. 29, 2008

(54) INFECTION-RESISTANT MEDICAL DEVICES

(75) Inventors: John Kenneth Gibson, Chesterfield, MO (US); Charles W. Ford, Portage, MI (US); Paul J. Pagano, Pinckney, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 575 days.

(21) Appl. No.: 10/348,066

(22) Filed: Jan. 21, 2003

(65) Prior Publication Data

US 2003/0176848 A1    Sep. 18, 2003

Related U.S. Application Data

(60) Provisional application No. 60/380,656, filed on May 15, 2002, provisional application No. 60/350,767, filed on Jan. 22, 2002.

(51) Int. Cl.
*A61M 25/00* (2006.01)
*A61M 5/32* (2006.01)

(52) U.S. Cl. .................................. 604/264

(58) Field of Classification Search ........... 604/500, 604/263, 265; 514/376; 427/2.28; 424/411, 424/422, 4
See application file for complete search history.

(56) References Cited

U.S. PATENT DOCUMENTS

| | | | | |
|---|---|---|---|---|
| 4,723,950 A | * | 2/1988 | Lee | .............. 604/322 |
| 5,055,455 A | * | 10/1991 | Pier | .............. 514/54 |
| 5,624,704 A | | 4/1997 | Darouichenet et al. | |
| 5,688,792 A | | 11/1997 | Barbachyn et al. | ...... 514/235.5 |
| 6,719,991 B2 | * | 4/2004 | Darouiche et al. | .......... 424/422 |
| 2003/0176848 A1 | | 9/2003 | Gibson | |
| 2003/0219461 A1 | | 11/2003 | Britten | |

FOREIGN PATENT DOCUMENTS

| RU | 2145961 | 2/2000 |
|---|---|---|
| WO | WO 95/21636 | 8/1995 |
| WO | WO 98/46287 | 10/1998 |
| WO | WO03007870 A2 | 1/2003 |
| WO | WO03061715 A1 | 7/2003 |
| WO | WO03097159 A1 | 11/2003 |
| WO | WO2004014392 A1 | 2/2004 |

OTHER PUBLICATIONS

Raad et al "*Staphylococcus epidermis*: Emerging Resistance and Need for Alternative Agents" (1998) Clinical Infectious Diseases. The University of Chicago 26: 1182-7.*

Lizondo et al. "Linezoid" Druges of the Future. (1996) Prous Science Publishers. 21(11): 1116-1123.*

Ford et al "In Vivo Activities of U-100592 and U-100766, Novel Oxazolidinone Antimicrobial Agents against Experimental Bacterial Infection" Jun. 1996 vol. 40 Issue 6. pp. 1508-1513.*

(Continued)

*Primary Examiner*—Catherine S. Williams
(74) *Attorney, Agent, or Firm*—Steve Zelson; Christian M. Smolizza

(57) ABSTRACT

A method for preventing medical device-associated microorganism infection includes the steps of providing a medical device and incorporating an effective amount of an oxazolidinone compound, such as linezolid, into the medical device.

10 Claims, 9 Drawing Sheets

Effects of subinhibitory concentrations of linezolid and vancomycin on adherence of *S. aureus* UC-20205 to polystyrene surfaces. Significant differences from control are indicated by an asterisk ($* = P \leq 0.05$). Data are from two experiments performed in triplicate.

OTHER PUBLICATIONS

International Preliminary Examination Report for Application No. PCT/US03/.01710 dated Jan. 28, 2004.

Written Opinion for Application No. PCT/US03/01710, dated Sep. 29, 2003.

International Search Report for Application No. PCT/US03/01710, dated May 19, 2003.

Paradisi, et al., "Antistaphylococcal (MSSA, MRSA, MSSE, MRSE) Antibiotics," in *Medical Clinics of North America*, Antibiotic Therapy, Part II, vol. 85, Jan. 2001.

"Linezolid: Oxazolidinone Antibacterial" in *Drugs of the Future*, vol. 21, 1996.

Raad, et al., "*Staphylococcus epidermis*: Emerging Resistance and Need for Alternative Agents," *Clinical Infectious Diseases*, 1998; 26: 1182-1187.

G. Zerah, et al., "Prevention of Infection Related to Pacemaker Implantation Using Laser Surgery and Prophylactic Antibiotics in a Series of 1184 Patients," *Pacing and Clinical Electrophysiology*, vol. 20, Part 2, Sep. 1, 1997.

National Committee for Clinical Laboratory Standards, *Methods for Dilution Antimicrobial Susceptibility Tests for Bacteria That Grow Aerobically; Approved Standard—Fifth Edition* (2000).

Mittelman, "Recovery and Characterization of Biofilm Bacteria Associated with Medical Devices," in *Methods in Enzymology*, vol. 310, Biofilms, 1999; 534-536.

Cramton, et al., "The Intercellular Adhesion (ica) Locus is Present in *Staphylococcus aureus* and Is Required for Biofilm Formation," *Infect. Immun.* 1999; 67:5427-5433.

Projan, et al., "The Molecular Basis of Pathogenicity," in *The Staphylococci in Human Disease*, 1997, 55-81.

Rupp, "Infections of Intravascular Catheters and Vascular Devices," in *The Staphylococci in Human Disease*, 1997; 379-399.

Mittelman, "Adhesion to Biomaterials," in *Bacterial Adhesion: Molecular and Ecological Diversity*, 1996; 89-127.

Costerton, "Introduction to Biofilm," *Int. J. Antimicrob. Agents*, 1999; 11:217-221.

Rupp, et al., "Characterization of the Importance of Polysaccharide Intercellular Adhesin/Hemagglutinin of *Staphylococcus epidermidis* in the Pathogenesis of Biomaterial-Based Infection in a Mouse Foreign Body Infection Model," *Infect. Immun.*, 1999; 67(5):2627-2632.

Gristina, "Biomaterial-Centered Infection: Microbial Adhesion Versus Tissue Integration," *Science*, 1987; 237:1588-1595.

Bisognano, et al., "Increases Expression of Fibronectin-Binding Proteins by Fluoroquinolone-Resistant *Staphylococcus aureus* Exposed to Subinhibitory Levels of Ciprofloxacin," *Antimicrob. Agents Chemother.*, 1997; 41(5):906-913.

Rupp, et al., "Characterization of *Staphylococcus epidermidis* Polysaccharide Intercellular Adhesin/Hemagglutinin in the Pathogenesis of Intravascular Catheter-Associated Infection in a Rat Model," *Infect. Immun.*, 1999; 67(5):2656-2659.

Clemett, et al., "Linezolid: New Drug Profile," *Drugs*, 2000; 59(4):815-827.

Shinabarger, "Mechanism of Action of the Oxazolidinone Antibacterial Agents," *Expert Opin. Invest. Drug.*, 1999; 8:1195-1202.

Davenport, et al., "Usefulness of a Test for Slime Production as a Marker for Clinically Significant Infections with Coagulase-Negative Staphyloccoci," *J. Infect. Dis.*, 1986; 153(2):332-339.

Deighton, et al., "Adherence Measured by Microtiter Assay as a Virulence Marker for *Staphylococcus epidermidis* Infections," *J. Clin. Microbiol.*, 1990; 28(11);2442-2447.

Christensen, et al., "Adherence of Coagulase-Negative Staphylococci to Plastic Tissue Culture Plates: A Quantitative Model for the Adherence of Staphylococci to Medical Devices," *J. Clin. Microbiol.*, 1985; 22(6):996-1006.

Khardori, et al., "Effect of Subinhibitory Concentrations of Clindamycin and Trospectomycin on the Adherence of *Staphylococcus epidermidis* in an In Vitro Model of Vascular Catheter Colonization," *J. Infect. Dis.*, 1991, 164:108-113.

Rachid, et al., "Effect of Subinhibitory Antibiotic Concentrations on Polysaccharide Intercellular Adhesin Expression in Biofilm-Forming *Staphylococcus epidermidis*," *Antimicrob. Agents Chemother.*, 2000; 44(12):3357-3363.

Schifferli, et al., "Bacterial Adhesion: Modulation by Antibiotics Which Perturb Protein Synthesis," *Antimicrob. Agents Chemother.*, 1988; 32(11):1603-1608.

Shibl, "Influence of Subinhibitory Concentrations of Antibiotics on Virulence of Staphylococci," *Rev. Infect. Dis.*, 1987; 9(4):704-712.

Carsenti-Etesse, et al., "Effects of Subinhibitory Concentrations of Vancomycin and Teicoplanin on Adherence of Staphylococci to Tissue Culture Plates," *Antimicrob. Agents Chemother.*, 1993; 37(4):921-923.

Rupp, et al., "Effect of Subinhibitory Concentrations of Vancomycin, Cefazolin, Ofloxacin, L-Ofloxacin and D-Ofloxacin on Adherence to Intravascular Catheters and Biofilm Formation by *Staphylococcus epidermidis*," *J. Antimicrob. Chemother.*, 1998; 41:155-161.

Schadow, et al., "Characteristics of Adherence to Plastic Tissue Culture Plates of Coagulase-Negative Staphylococci Exposed to Subinhibitory Concentrations of Antimicrobial Agents," *J. Infect. Dis.*, 1988; 157(1):71-77.

Wilcox et al., "Effects of Carbon Dioxide and Sub-Lethal Levels of Antibiotics on Adherence of Coagulase-Negative Staphylococci to Polystyrene and Silicone Rubber," *J. Antimicrob. Chemother.* 1991; 27:577-587.

Mermei, L A. et al., Guildelines for the Management fo Intravascular Catheter-Related Infections, Clinical Infectious Deseases, 2001: 32:1249-72.

Cammarata, Sue K et al., Incidence of intravenous catheter-related complications during clinical trials of linezolid, an oxazolidinone., Clinical Infectious Diseases, 31(1), Jul. 2000. 225.

Leach T S et al, Clinical efficacy of linezolid for infections caused by vancomycin-resistant enterococci (VRE) in a compassionate-use program. Clinical Infectious Diseases. vol. 31(1), 224, 2000.

Birmingham M C et al., Treating outpatients (outpts) with significant, resistant Gram-positive infectious with linezolid (LNZ). Clinical Infectious Diseases, vol. 31(1), 224, 2000.

Chien J W et al., Use of linezolid, an oxazolidinone, in the treatment of multidrug-resistant gram-positive bacterial infections. Clinical Infectious Diseases vol. 30(1), pp. 146-151, 2000.

McNeil S A et al., Successful treatment of vancomycin-resistant *Enterococcus faecium* bacteremia with linezolid after failure of treatment with Synercid (quinupristin/dalfopristin). Clinical Infectious Diseases, vol. 30(2) pp. 403-404, 2000.

Smith P F, et al., Clinical outcomes (CO), safety and tolerance of linezolid (LZD) for resistant Gram-positive (G+) infections in patients with neutropenia. Clinical Infectious Diseases, vol. 29(4), p. 960, 1999.

McGahee W, et al., Staphylococcal infections in the intensive care unit. Seminars in Respiratory Infections, vol. 15(4), pp. 308-313, 2000.

Wilcox M H, et al., In situ measurement of linezolid and vancomycin concentrations in intravascular catheter-associated biofilm. Journal of Antimicrobial Chemotherapy, vol. 47, pp. 171-175, 2001.

Wilcox M H, et al., Abstr Measurement of Linezolid and Vancomycin Concentrations and Bacterial Killing in Intravascular Catheter Associated Biofilm. vol. 40:34, pp. 17-20; Sep. 2000.

Pagano, P.J., et al., Effects of Linezolid on staphylococcal adherence versus time of treatment. International Journal of Antimicrobial Agents, 23 (2004) 226-234.

Zimmerli, W. et al., Role of Rifampin for Treatment of Orthopedic Implant-Related Staphylococcal Infections., JAMA, May 20, 1998 vol. 279, No. 19, pp. 1537-1541.

Zimmerli, W., et al., Reconsideration of Rifampin, JAMA, May 20, 1998, vol. 279, No. 19, pp. 1575-1577.

Hanna, H.A., et al., Antibiotic-Impregnated Catheters Associated With Significant Decrease in Nosocomial and Multidrug-Resistant bacteremias in Critically Ill Patients., Clinical Investigations in Critical Care, 124, vol. 3, Sep. 2003, pp. 1031-1038.

Gander, S., et al., An investigation of the antimicrobial effects of linezolid of bacterial biofilms utilizing an invitro pharmacokinetic model., Journal of Antimicrbial Chemotherapy, (2002) 49, pp. 301-308.

Mader, J.T., et al., In Vitro Evaluation of Antibiotic Diffusion form Antibiotic-Impregnated Biodegradable Beads and Polymethylmethacrylate Beads., Antimicrobial Agents in Chemotherapy, Feb. 1997, Vo. 4, No. 2, pp. 415-418.

Elliott, T.S., Role of antimicrobial central venous catheters for the prevention of associated infections., Journal of Antimicrobial Chemotherapy (1999) 43, pp. 441-446.

Cimbollek, M., et al., Antibiotic-Impregnated Heart Valve Sewing Rings for Treatment and Prophylaxis of Bacterial Endocarditis., Antimicrobial Agents and Chemotherapy, Jun. 1996, vol. 40 No. 6, pp. 1432-1437.

Raad, I., et al., Antibiotics and Prevention of Microbial Colonization of Catheters., Antimicrobial Agents and Chemotherapy., Nov. 1995, Vo. 39, No. 11., pp. 2397-2400.

Bassetti, S., et al., Prolonged Antimicrobial Acrivity of a Catheter Containing Chlorhexidine-Silver Sulfadiazine Extends Protection against Catheter Infections In Vivo., Antimicrobial Agents and Chemotherapy, May 2001, vol. 45, No. 5 pp. 1535-1538.

Dailey CF, Buchanan et al., Efficacy of PNU-288034 in the Treatment of Experimental Methicillin-Resistant *Staphylococcus aureus* (MRSA) Endocarditis, Propgram and Abstracts of the 42nd Interscience Conferences Sept. 29, 2002. San Diego CA., American Society for Microbiology; 2002 abstract No. F1-1340.

Gibson, JK, et al., Anti-adhesion effects of linezolid on staphylococcal isolates from patients with catheter-related bloodstream infections in: Program and Abstracts of the 42nd Intersicen Conferences on Antimicrobial Agents and Chemotherapy, Sep. 29, 2002, San Diego CA, Wash. D.C., American Society for Microbiology; 2002 [Abstract No. C1-1606].

\* cited by examiner

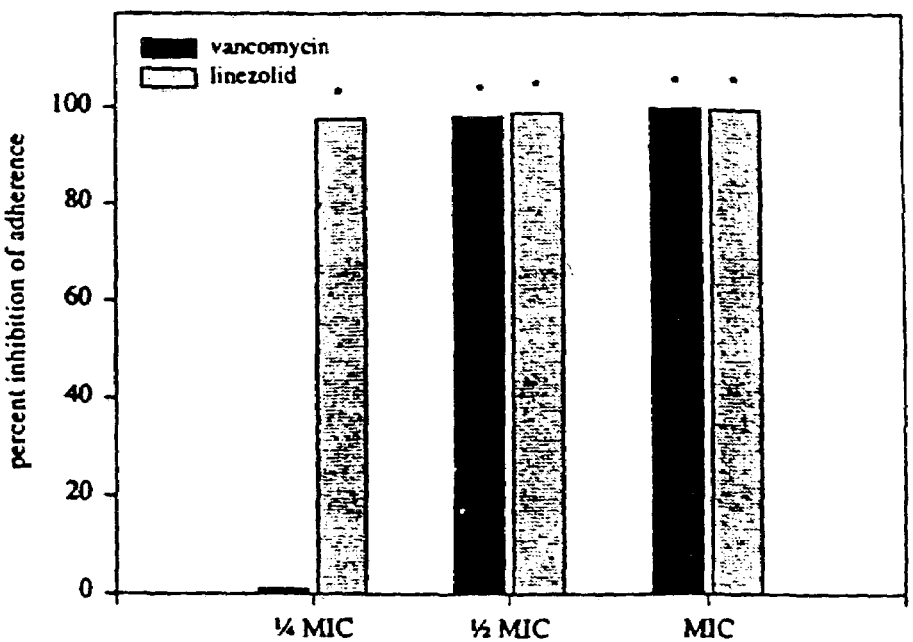

Figure 1. Effects of subinhibitory concentrations of linezolid and vancomycin on adherence of *S. aureus* UC-20205 to polystyrene surfaces. Significant differences from control are indicated by an asterisk (* = $P \leq 0.05$). Data are from two experiments performed in triplicate.

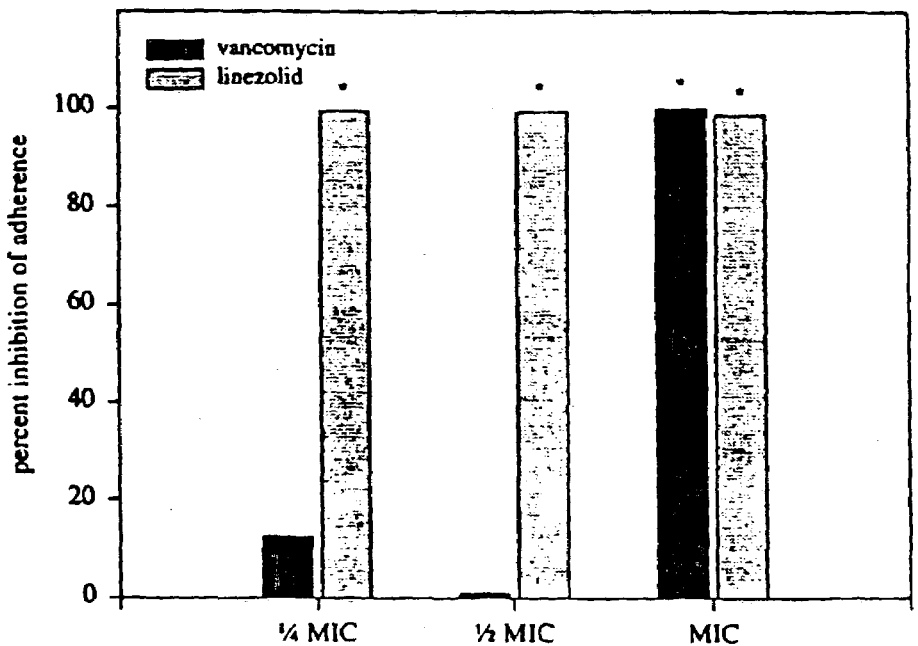

Figure 2. Effects of subinhibitory concentrations of linezolid and vancomycin on adherence of *S. aureus* UC-20206 to polystyrene surfaces. Significant differences from control are indicated by an asterisk (* = $P \leq 0.05$). Data are from two experiments performed in triplicate.

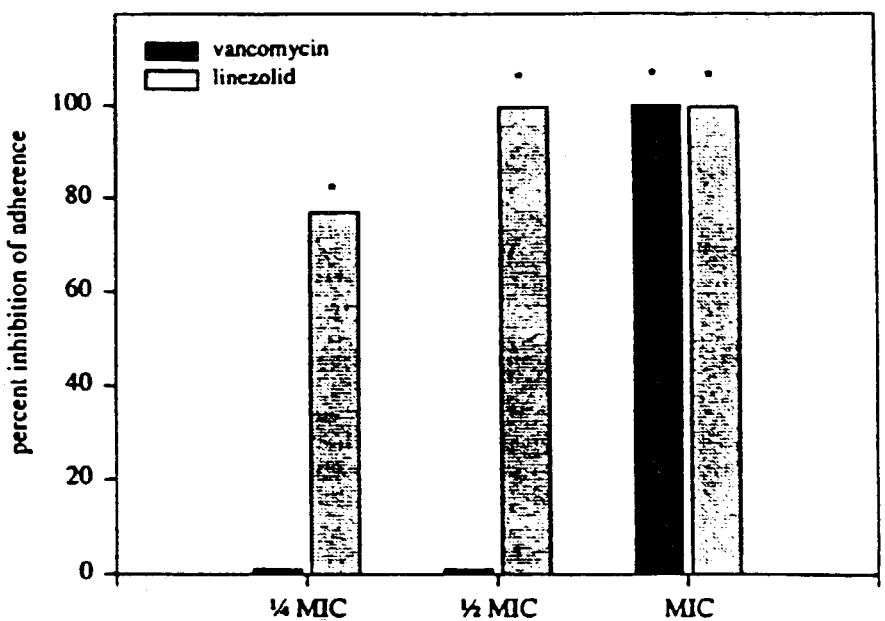

Figure 3. Effects of subinhibitory concentrations of linezolid and vancomycin on adherence of S. epidermidis UC-20207 to polystyrene surfaces. Significant differences from control are indicated by an asterisk (* = P ≤ 0.05). Data are from two experiments performed in triplicate.

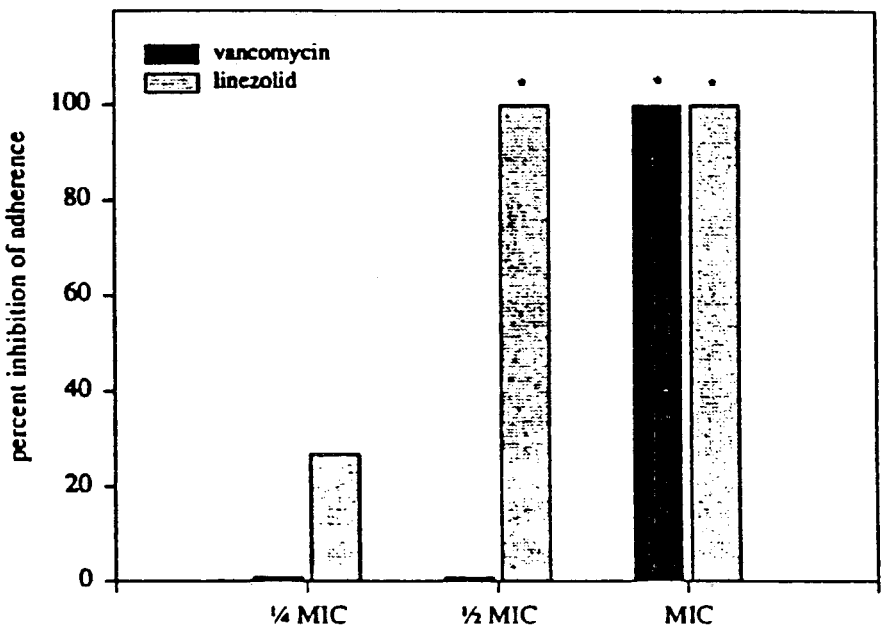

Figure 4. Effects of subinhibitory concentrations of linezolid and vancomycin on adherence of S. epidermidis UC-20208 to polystyrene surfaces. Significant differences from control are indicated by an asterisk (* = P ≤ 0.05). Data are from two experiments performed in triplicate.

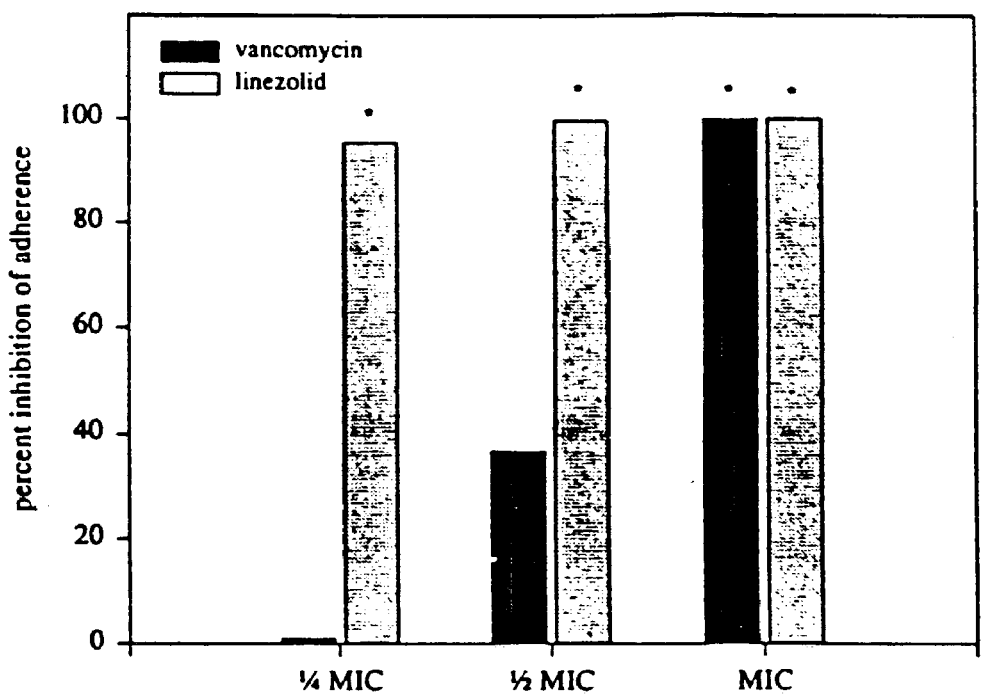
Figure 5. Effects of subinhibitory concentrations of linezolid and vancomycin on adherence of S. epidermidis RP62A to polystyrene surfaces. Significant differences from control are indicated by an asterisk (* = P ≤ 0.05). Data are from two experiments performed in triplicate.

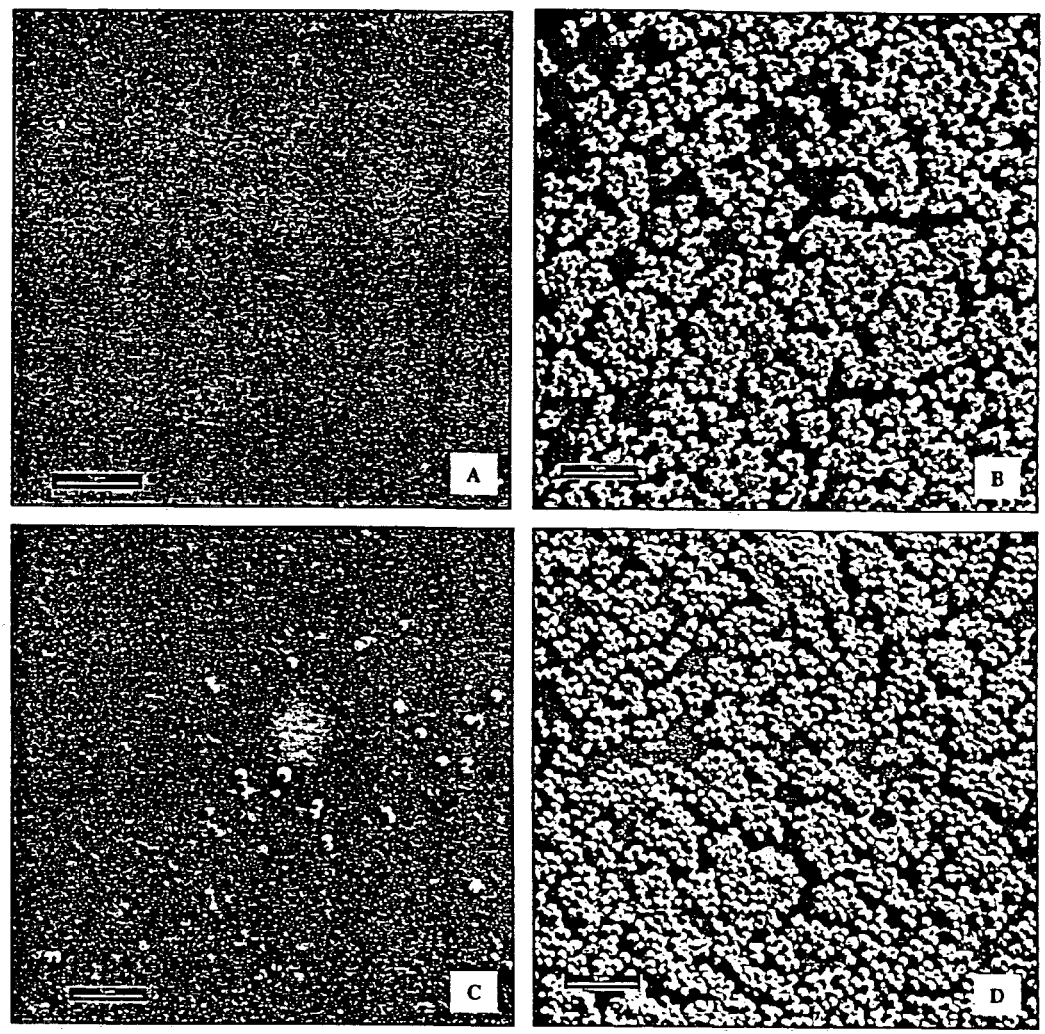
Figure 6. Scanning electron micrographs showing microcolonies of *S. aureus* UC-20205 adherent to the surface of polystyrene. Noninfected control (A), infected-nontreated control (B), infected culture treated with linezolid at one-fourth the MIC (C), and infected culture treated with vancomycin at one-fourth the MIC (D).
bar = 5μm

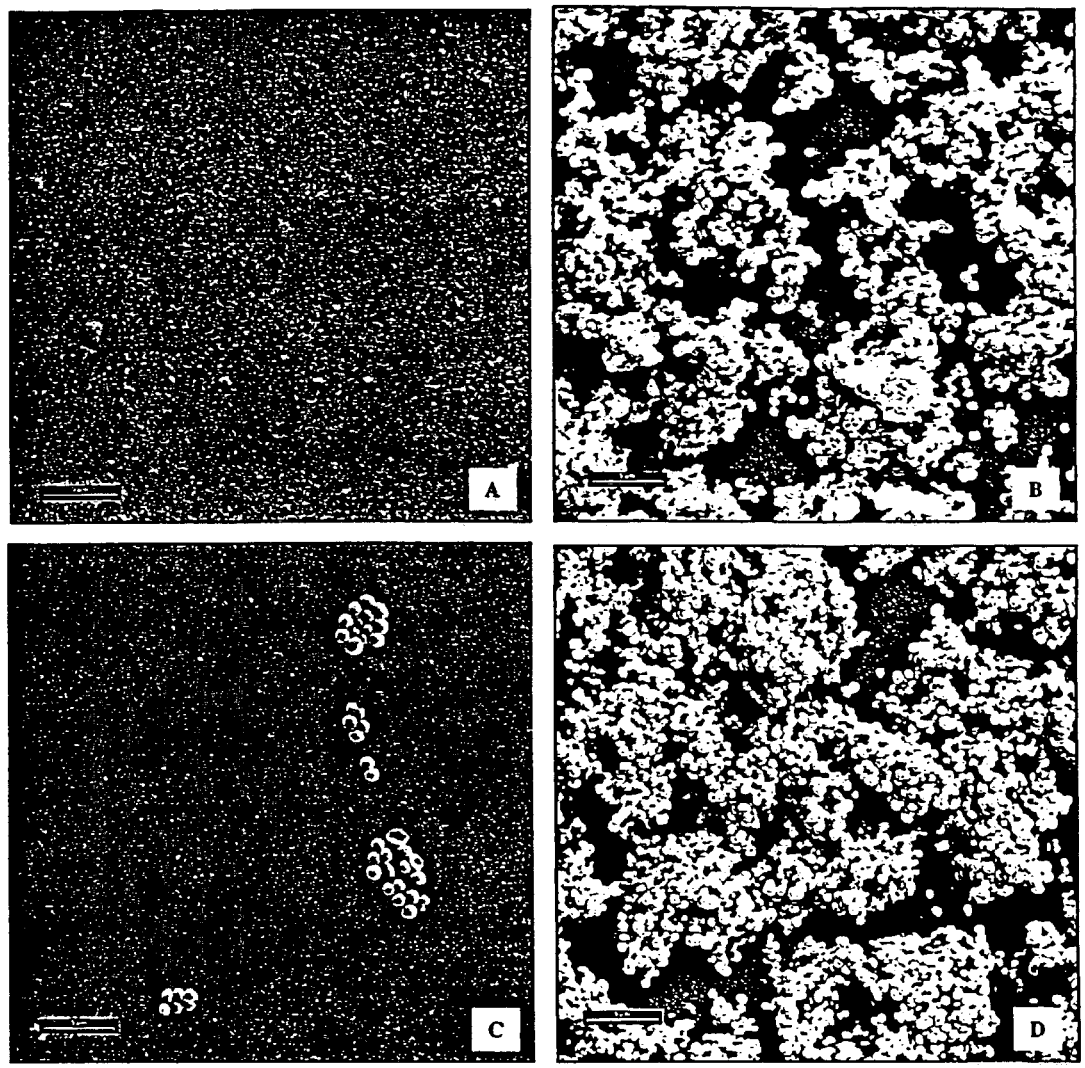
Figure 7. Scanning electron micrographs showing microcolonies of *S. epidermidis* RP62A adherent to the surface of polystyrene. Noninfected control (A), infected-nontreated control (B), infected culture treated with linezolid at one-fourth the MIC (C), and infected culture treated with vancomycin at one-fourth the MIC (D).
bar = 5μm

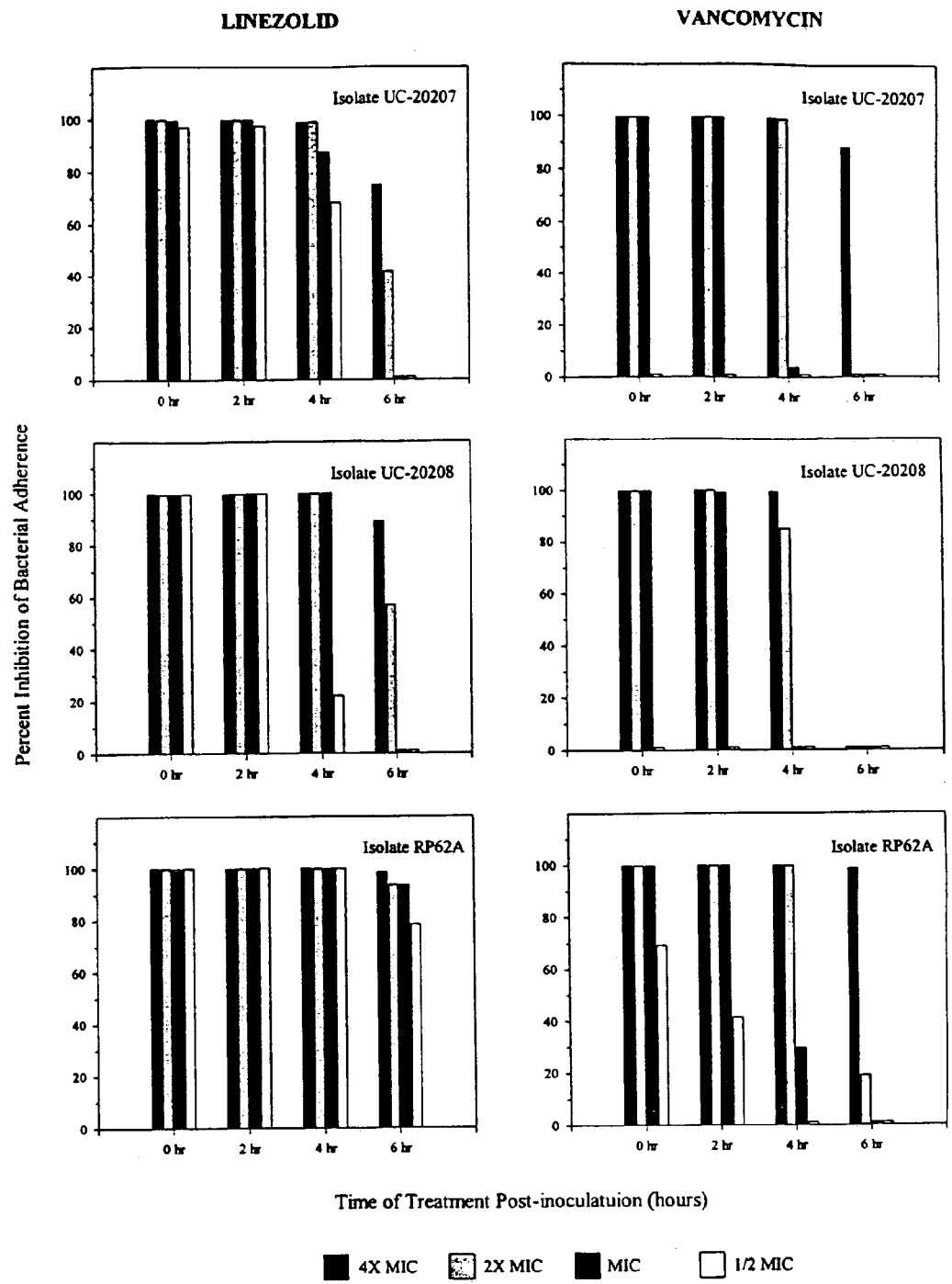
Figure 8. Inhibitory effects of prophylactic and delayed treatments with therapeutic (≥MIC) and subtherapeutic (1/2 MIC) concentrations of linezolid or vancomycin on staphylococcal adherence to polystyrene surfaces. Data are from two experiments performed in triplicate.

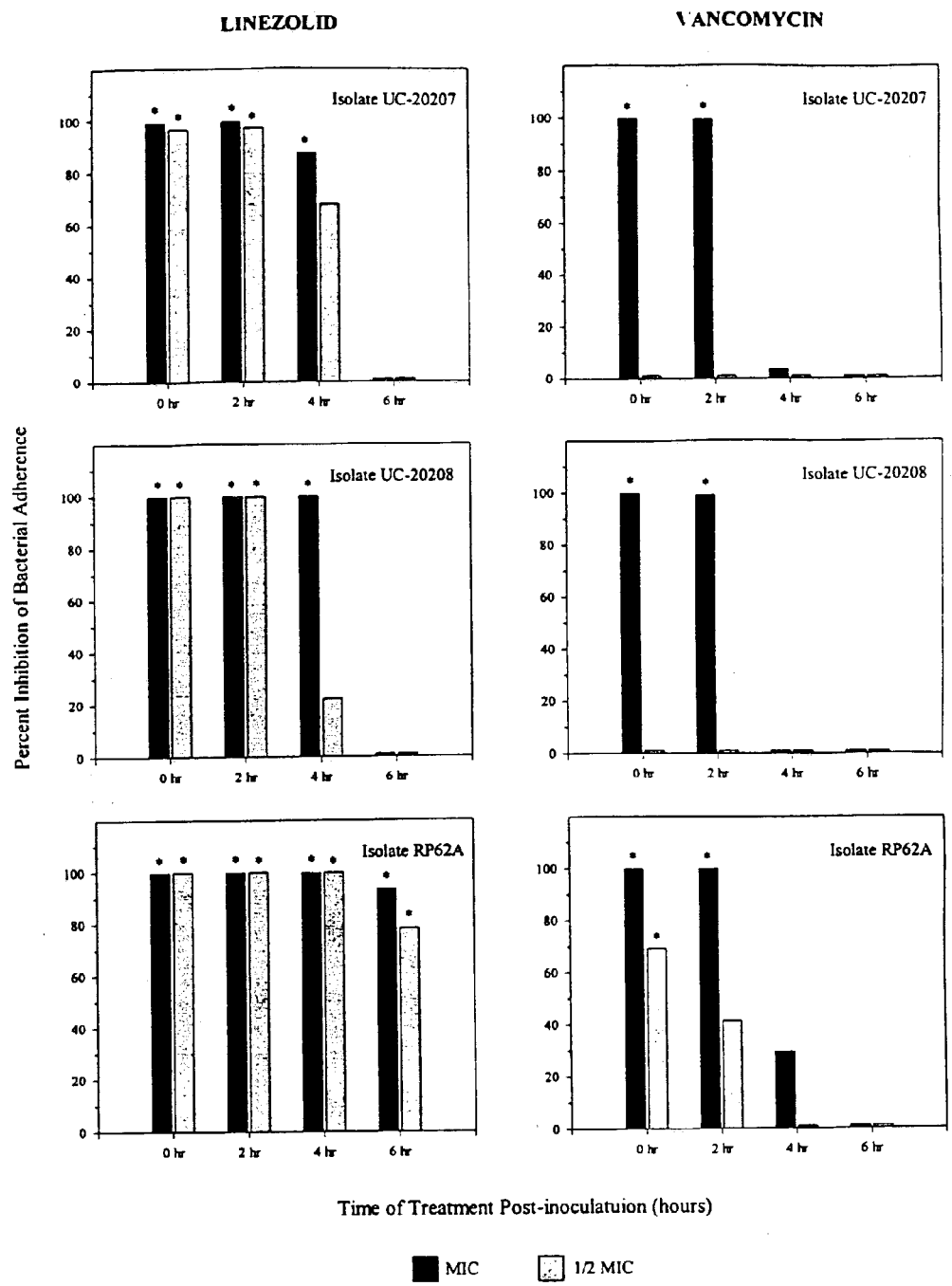
Figure 9. Inhibitory effects of prophylactic and delayed treatments with MIC and sub-MIC (1/2) levels of linezolid or vancomycin on staphylococcal adherence to polystyrene surfaces. Significant differences from control are indicated by an asterisk (* = $p<0.05$). Data are from two experiments performed in triplicate.

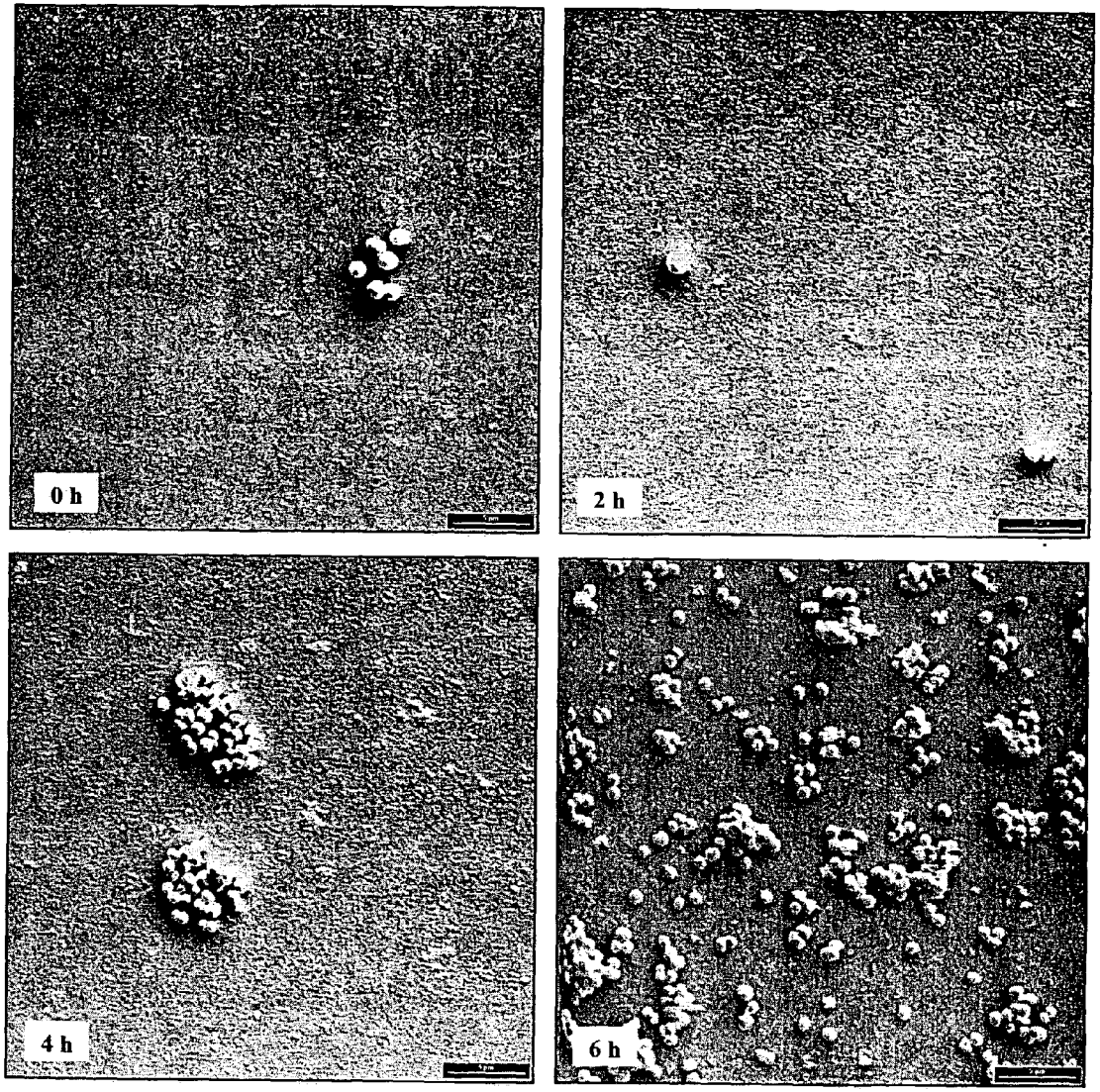
Figure 10. Scanning electron micrographs showing the effects of prophylactic (0 h) and delayed (2 h, 4 h, and 6 h) treatments with 1 µg/ml of linezolid (½ MIC) on *S. epidermidis* RP62A microcolonies adherent to the surface of polystyrene.
bar = 5 µm

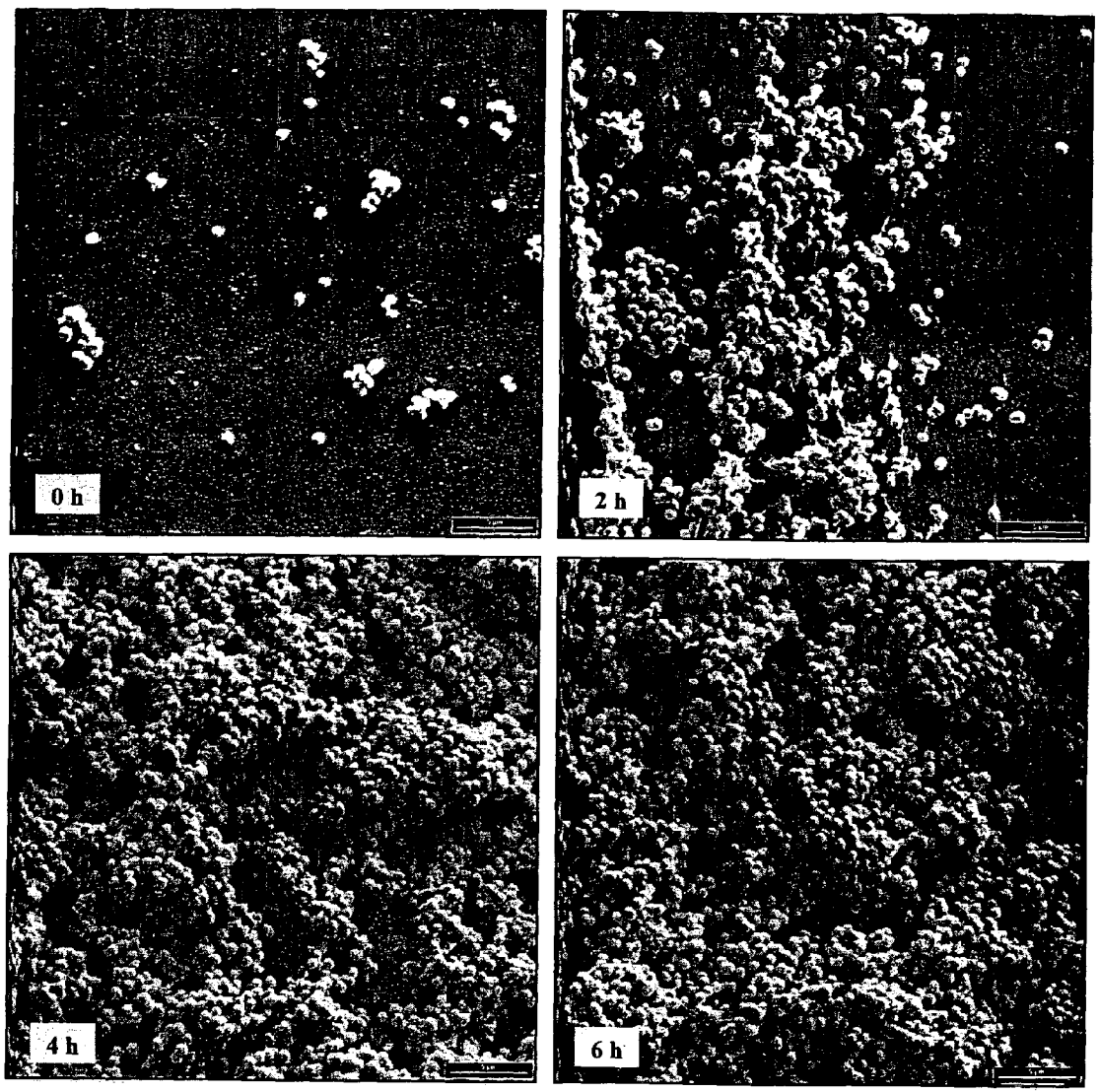
Figure 11. Scanning electron micrographs showing the effects of prophylactic (0 h) and delayed (2 h, 4 h, and 6 h) treatments with 1 µg/ml of vancomycin (½ MIC) on *S. epidermidis* RP62A microcolonies adherent to the surface of polystyrene.
bar = 5 µm

INFECTION-RESISTANT MEDICAL DEVICES

CROSS REFERENCE TO RELATED APPLICATIONS

This application claims the benefit of U.S. provisional patent application Ser. No. 60/380,656, filed May 15, 2002, and U.S. provisional patent application Ser. No. 60/350,767, filed Jan. 22, 2002.

BACKGROUND OF THE INVENTION

1. Field of the Invention

The invention relates generally to prohibiting microorganism infection associated with implanted medical devices. In particular, the invention relates to the use of oxazolidinone compounds such as linezolid to prevent medical device-associated infections.

2. Description of Related Technology

Implantable medical devices made of biomaterials (i.e., biologically-compatible materials known to those skilled in the art, such as metal, polymeric, or ceramic materials) are frequently used for treatment of a variety of human diseases and other conditions. Growth of microorganisms on the surfaces of such medical devices following implantation occurs relatively infrequently, but can produce serious and costly complications, such as requiring removal or replacement of the implanted device or vigorous treatment of secondary infections.

Advances in engineered materials and surgical techniques coupled with the demographics of an aging population suggest an increasing demand for implantable medical devices over the next several decades. Implantable devices include, for example, sutures, orthopedic appliances, stents, catheters, guidewires, shunts (e.g., hemodialysis shunts or cerebrospinal shunts), prostheses (e.g., prosthetic heart valves or prosthetic joints), cardiac pacemakers, neuronal stimulators, and vascular grafts. However, a major limiting factor in the use of implantable devices is the risk of microbial growth on the biomaterials by microbes, such as bacteria, to form biofilms, which may cause serious infections, such as osteomyelitis, endocarditis, or septic shock. Such infections can occur despite the prophylactic administration of antibiotics in implantation surgery, which has become standard practice for such surgeries.

Consequently, effective treatment of infections often necessitates the removal of the implanted device. Accordingly, there is a need for improved methods for prevention of medical device-associated infections.

SUMMARY OF THE INVENTION

In general, the invention relates to methods of preventing infection associated with medical devices by inhibiting bacterial adherence to the surface of the device.

According to one aspect of the present invention, a method for preparing an infection-resistant medical device for use within a human or animal body includes the steps of providing a medical device and incorporating an effective amount of an antimicrobial agent comprising an oxazolidinone compound into the medical device.

According to another aspect of the invention, a method of inhibiting adherence of bacteria to a medical device includes the steps of providing an antibacterial agent comprising linezolid, or a pharmaceutically acceptable salt thereof, and incorporating the antibacterial agent into the medical device.

According to still another aspect of the invention, a method of inhibiting bacterial adherence to an implanted medical device includes the steps of implanting a medical device in a human or animal body, and applying an antibacterial agent comprising an oxazolidinone, or a pharmaceutically acceptable salt thereof, to the implanted medical device.

According to yet another aspect of the invention, a method of inhibiting bacterial adherence to an implanted medical device includes the steps of administering a pharmaceutical composition comprising an oxazolidinone, or a pharmaceutically acceptable salt thereof, to a patient in need of an implanted medical device, and implanting a medical device in the patient.

According to a further aspect of the invention, a medical device resistant to microbial adherence for use within a human or animal body includes an effective amount of linezolid, or a pharmaceutically acceptable salt thereof.

These and other aspects and advantages of the invention will be apparent from the following detailed description.

BRIEF DESCRIPTION OF THE DRAWINGS

FIG. 1 is a graph illustrating effects of subinhibitory concentrations (less than the minimum inhibitory concentration) of linezolid and vancomycin on adherence of *S. aureus* UC-20205 to polystyrene surfaces;

FIG. 2 is a graph illustrating effects of subinhibitory concentrations of linezolid and vancomycin on adherence of *S. aureus* UC-20206 to polystyrene surfaces;

FIG. 3 is a graph illustrating effects of subinhibitory concentrations of linezolid and vancomycin on adherence of *S. epidermidis* UC-20207 to polystyrene surfaces;

FIG. 4 is a graph illustrating effects of subinhibitory concentrations of linezolid and vancomycin on adherence of *S. epidermidis* UC-20208 to polystyrene surfaces;

FIG. 5 is a graph illustrating effects of subinhibitory concentrations of linezolid and vancomycin on adherence of *S. epidermidis* RP62A to polystyrene surfaces;

FIGS. 6A-D are scanning electron micrographs showing microcolonies of *S. aureus* UC-20205 adherent to a polystyrene surface: (A) noninfected control; (B) infected-non-treated control; (C) infected culture treated with linezolid at one-fourth the MIC; and (D) infected culture treated with vancomycin at one-fourth the MIC; and FIGS. 7A-D are scanning electron micrographs showing microcolonies of *S. epidermidis* RP62A adherent to a polystyrene surface: (A) noninfected control; (B) infected-non-treated control; (C) infected culture treated with linezolid at one-fourth the MIC; and (D) infected culture treated with vancomycin at one-fourth the MIC.

FIG. 8 shows graphs of the inhibitory effects of prophylactic and delayed treatments with therapeutic (equal to or greater than the MIC) and subtherapeutic (one-half the MIC) concentrations of linezolid or vancomycin on *staphylococcal* adherence to polystyrene surfaces as detailed in Table 4.

FIG. 9 shows graphs of the inhibitory effects of prophylactic and delayed treatments with MIC and sub-MIC (one-half MIC) levels of linezolid or vancomycin on staphylococcal adherence to polystyrene surfaces as detailed in Table 5. Significant differences from control are indicated by an asterisk (*=$p<0.05$).

FIG. 10 shows scanning electron micrographs exhibiting the effects of prophylactic (0 h) and delayed (2 h, 4 h, and 6 h) treatments with 1 μg/ml of linezolid (one-half MIC) on *S. epidermidis* RP62A microcolonies adherent to the surface of polystyrene.

FIG. 11 shows scanning electron micrographs showing the effects of prophylactic (0 h) and delayed (2 h, 4 h, and 6 h) treatments with 1 μg/ml of vancomycin (one-half MIC) on *S. epidermidis* RP62A microcolonies adherent to the surface of polystyrene.

DETAILED DESCRIPTION OF THE INVENTION

Oxazolidinones are a class of synthetic antibacterial agents. Oxazolidinone compounds are known in the art. In some embodiments, oxazolidinone compounds may have the formula:

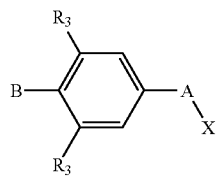

I or a pharmaceutically acceptable salt thereof wherein:

A is a structure i, ii, iii, or iv

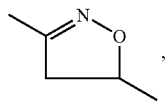

i

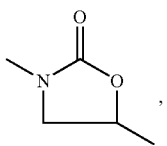

ii

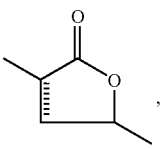

iii

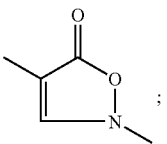

iv

B is selected from cycloalkyl, substituted cycloalkyl, cycloalkenyl, substituted cycloalkenyl, aryl, substituted aryl, het and substituted het, or B and one $R_3$ together, with the phenyl carbon atoms to which B and the one $R_3$ are bonded, form a het, the het optionally being a substituted het;

X is a group selected from —$CH_2$—NH—C(O)—$R_4$, —$CH_2$—$R_4$, and —$CH_2$—Y—$R_4$;

Each Y is O, S, or —NH—;

Each of $R_1$ and $R_2$ is independently selected from H, —OH, amino, alkyl, alkoxy, alkenyl, substituted amino, substituted alkyl, substituted alkoxy, and substituted alkenyl;

Each $R_3$ is independently selected from H, alkyl, alkoxy, amino, $NO_2$, CN, halo, substituted alkyl, substituted alkoxy, and substituted amino; and Each $R_4$ is independently selected from H, —OH, amino, alkyl, substituted alkyl, alkoxy, substituted alkoxy, alkenyl, substituted alkenyl, cycloalkyl, substituted cycloalkyl, cycloalkenyl, substituted cycloalkenyl, het, substituted het, aryl, and substituted aryl.

The following definitions are used, unless otherwise described.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$ alkyl refers to alkyl of one to seven carbon atoms, inclusive.

The term "halo" refers to a halogen atom selected from Cl, Br, I, and F.

The term "alkyl" refers to both straight- and branched-chain moieties. Unless otherwise specifically stated alkyl moieties include between 1 and 6 carbon atoms.

The term "alkenyl" refers to both straight- and branched-chain moieties containing at least one —C=C—. Unless otherwise specifically stated alkenyl moieties include between 1 and 6 carbon atoms.

The term "alkynyl" refers to both straight- and branched-chain moieties containing at least one —C/C—. Unless otherwise specifically stated alkynyl moieties include between 1 and 6 carbon atoms. between 1 and 6 carbon atoms The term "alkoxy" refers to —O-alkyl groups.

The term "cycloalkyl" refers to a cyclic alkyl moiety. Unless otherwise specifically stated cycloalkyl moieties will include between 3 and 9 carbon atoms.

The term "cycloalkenyl" refers to a cyclic alkenyl moiety. Unless otherwise specifically stated cycloalkyl moieties will include between 3 and 9 carbon atoms and at least one —C=C— group within the cyclic ring.

The term "amino" refers to —$NH_2$.

The term "aryl" refers to phenyl, phenyl, and naphthyl.

The term "het" refers to mono- or bi-cyclic ring systems containing at least one heteroatom selected from O, S, and N. Each mono-cyclic ring may be aromatic, saturated, or partially unsaturated. A bi-cyclic ring system may include a mono-cyclic ring containing at least one heteroatom fused with a cycloalkyl or aryl group. A bi-cyclic ring system may also include a mono-cyclic ring containing at least one heteroatom fused with another het, mono-cyclic ring system.

Examples of "het" include, but are not limited to, pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl, 5-isothiazolyl, 1,3,4,-oxadiazole, 4-oxo-2-thiazolinyl, 5-methyl-1,3,4-thiadiazol-2-yl, thiazoledione, 1,2,3,4-thiatriazole, 1,2,4-dithiazolone, phthalimide, quinolinyl, morpholinyl, benzoxazoyl, diazinyl, triazinyl, quinolinyl, quinoxalinyl, naphthyridinyl, azetidinyl, pyrrolidinyl, hydantoinyl, oxathiolanyl, dioxolanyl, imidazolidinyl, and azabicyclo[2.2.1]heptyl.

The term "substituted alkyl" refers to an alkyl moiety including 1-4 substituents selected from halo, het, cycloalkyl, cycloalkenyl, aryl, —$OQ_{10}$, —$SQ_{10}$, —$S(O)_2Q_{10}$, —$S(O)Q_{10}$, —$OS(O)_2Q_{10}$, —$C(=NQ_{10})Q_{10}$, —$SC(O)Q_{10}$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(O)C(Q_{16})_2OC(O)Q_{10}$, —CN, =O, =S, —$NQ_{10}C(O)Q_{10}$, —$NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, —$NQ_{10}SQ_{10}$, —$NO_2$, and —$SNQ_{10}Q_{10}$. Each of the het, cycloalkyl, cycloalkenyl, and aryl being optionally substituted with 1-4 substituents independently selected from halo $Q_{15}$.

The term "substituted aryl" refers to an aryl moiety having 1-3 substituents selected from —$OQ_{10}$, —$SQ_{10}$, —$S(O)_2Q_{10}$, —$S(O)Q_{10}$, —$OS(O)_2Q_{10}$, —$C(=NQ_{10})Q_{10}$, —$SC(O)Q_{10}$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(O)C(Q_{16})_2OC(O)Q_{10}$, —CN, —$NQ_{10}C(O)Q_{10}$, —$NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, —$NQ_{10}SQ_{10}$, —$NO_2$, —$SNQ_{10}Q_{10}Q_{10}$, alkyl, substituted alkyl, het, halo, cycloalkyl, cycloalkenyl, and aryl. The het, cycloalkyl, cycloalkenyl, and aryl being optionally substituted with 1-3 substituents selected from halo and $Q_{15}$.

The term "substituted het" refers to a het moiety including 1-4 substituents selected from —$OQ_{10}$, —$SQ_{10}$, —$S(O)_2Q_{10}$, —$S(O)Q_{10}$, —$OS(O)_2Q_{10}$, —$C(=NQ_{10})Q_{10}$, —$SC(O)Q_{10}$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(O)C(Q_{16})_2OC(O)Q_{10}$, —CN, =O, =S, —$NQ_{10}C(O)Q_{10}$, —$NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, —$NQ_{10}SQ_{10}$, —$NO_2$, —$SNQ_{10}Q_{10}$, alkyl, substituted alkyl, het, halo, cycloalkyl, cycloalkenyl, and aryl. The het, cycloalkyl, cycloalkenyl, and aryl being optionally substituted with 1-3 substituents selected from halo and $Q_{15}$.

The term "substituted alkenyl" refers to a alkenyl moiety including 1-3 substituents —$OQ_{10}$, —$SQ_{10}$, —$S(O)_2Q_{10}$, —$S(O)Q_{10}$, —$OS(O)_2Q_{10}$, —$C(=NQ_{10})Q_{10}$, —$SC(O)Q_{10}$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(O)C(Q_{16})_2OC(O)Q_{10}$, —CN, =O, =S, —$NQ_{10}C(O)Q_{10}$, —$NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, —$NQ_{10}SQ_{10}$, —$NO_2$, —$SNQ_{10}Q_{10}$, alkyl, substituted alkyl, het, halo, cycloalkyl, cycloalkenyl, and aryl. The het, cycloalkyl, cycloalkenyl, and aryl being optionally substituted with 1-3 substituents selected from halo and $Q_{15}$.

The term "substituted alkoxy" refers to an alkoxy moiety including 1-3 substituents —$OQ_{10}$, $SQ_{10}$, —$S(O)_2Q_{10}$, —$S(O)Q_{10}$, —$OS(O)_2Q_{10}$, —$C(=NQ_{10})Q_{10}$, —$SC(O)Q_{10}$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(O)C(Q_{16})_2OC(O)Q_{10}$, —CN, =O, =S, —$NQ_{10}C(O)Q_{10}$, —$NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, —$NQ_{10}SQ_{10}$, —$NO_2$, —$SNQ_{10}Q_{10}$, alkyl, substituted alkyl, het, halo, cycloalkyl, cycloalkenyl, and aryl. The het, cycloalkyl, cycloalkenyl, and aryl being optionally substituted with 1-3 substituents selected from halo and $Q_{15}$.

The term "substituted cycloalkenyl" refers to a cycloalkenyl moiety including 1-3 substituents —$OQ_{10}$, —$SQ_{10}$, —$S(O)_2Q_{10}$, —$S(O)Q_{10}$, —$OS(O)_2Q_{10}$, —$C(=NQ_{10})Q_{10}$, —$SC(O)Q_{10}$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(O)C(Q_{16})_2OC(O)Q_{10}$, —CN, =O, =S, —$NQ_{10}C(O)Q_{10}$, —$NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, —$NQ_{10}SQ_{10}$, —$NO_2$, —$SNQ_{10}Q_{10}$, alkyl, substituted alkyl, het, halo, cycloalkyl, cycloalkenyl, and aryl. The het, cycloalkyl, cycloalkenyl, and aryl are being optionally substituted with 1-3 substituents selected from halo and $Q_{15}$.

The term "substituted amino" refers to an amino moiety in which one or both of the amino hydrogens are replaced with a group selected from —$OQ_{10}$, —$SQ_{10}$, —$S(O)_2Q_{10}$, —$S(O)Q_{10}$, —$OS(O)_2Q_{10}$, —$C(=NQ_{10})Q_{10}$, —$SC(O)Q_{10}$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(O)C(Q_{16})_2OC(O)Q_{10}$, —CN, =O, =S, —$NQ_{10}C(O)Q_{10}$, —$NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, —$NQ_{10}SQ_{10}$, —$NO_2$, —$SNQ_{10}Q_{10}$, alkyl, substituted alkyl, het, halo, cycloalkyl, cycloalkenyl, and aryl. The het, cycloalkyl, cycloalkenyl, and aryl being optionally substituted with 1-3 substituents selected from halo and $Q_{15}$.

Each $Q_{10}$ is independently selected from —H, alkyl, cycloalkyl, het, cycloalkenyl, and aryl. The het, cycloalkyl, cycloalkenyl, and aryl being optionally substituted with 1-3 substituents selected from halo and $Q_{13}$.

Each $Q_{11}$ is independently selected from —H, halo, alkyl, aryl, cycloalkyl, and het. The alkyl, aryl, cycloalkyl, and het being optionally substituted with 1-3 substituents independently selected from halo, —$NO_2$, —CN, =S, =O, and $Q_{14}$.

Each $Q_{13}$ is independently selected from $Q_{11}$, —$OQ_{11}$, —$SQ_{11}$, —$S(O)_2Q_{11}$, —$S(O)Q_{11}$, —$OS(O)_2Q_{11}$, —$C(=NQ_{11})Q_{11}$, —$SC(O)Q_{11}$, —$NQ_{11}Q_{11}$, —$C(O)Q_{11}$, —$C(S)Q_{11}$, —$C(O)OQ_{11}$, —$OC(O)Q_{11}$, —$C(O)NQ_{11}Q_{11}$, —$C(O)C(Q_{16})_2OC(O)Q_{10}$, —CN, =O, =S, —$NQ_{11}C(O)Q_{11}$, —$NQ_{11}C(O)NQ_{11}Q_{11}$, —$S(O)_2NQ_{11}Q_{11}$, —$NQ_{11}S(O)_2Q_{11}$, —$NQ_{11}S(O)Q_{11}$, —$NQ_{11}SQ_{11}$, —$NO_2$, and —$SNQ_{11}Q_{11}$.

Each $Q_{14}$ is —H or a substituent selected from alkyl, cycloalkyl, cycloalkenyl, phenyl, or naphthyl, each optionally substituted with 1-4 substituents independently selected from —F, —Cl, —Br, —I, —$OQ_{16}$, —$SQ_{16}$, —$S(O)_2Q_{16}$, —$S(O)Q_{16}$, —$OS(O)_2Q_{16}$, —$NQ_{16}Q_{16}$, —$C(O)Q_{16}$, —$C(S)Q_{16}$, —$C(O)OQ_{16}$, —$NO_2$, —$C(O)NQ_{16}Q_{16}$, —CN, —$NQ_{16}C(O)Q_{16}$, —$NQ_{16}C(O)NQ_{16}Q_{16}$, —$S(O)_2NQ_{16}Q_{16}$, and —$NQ_{16}S(O)_2Q_{16}$. The alkyl, cycloalkyl, and cycloalkenyl being further optionally substituted with =O or =S.

Each $Q_{15}$ is alkyl, cycloalkyl, cycloalkenyl, het, phenyl, or naphthyl, each optionally substituted with 1-4 substituents independently selected from —F, —Cl, —Br, —I, —$OQ_{16}$, —$SQ_{16}$, —$S(O)_2Q_{16}$, —$S(O)Q_{16}$, —$OS(O)_2Q_{16}$, —$C(=NQ_{16})Q_{16}$, —$SC(O)Q_{16}$, —$NQ_{16}Q_{16}$, —$C(O)Q_{16}$, —$C(S)Q_{16}$, —$C(O)OQ_{16}$, —$OC(O)Q_{16}$, —$C(O)NQ_{16}Q_{16}$, —$C(O)C(Q_{16})_2OC(O)Q_{16}$, —CN, —$NQ_{16}C(O)Q_{16}$, —$NQ_{16}C(O)NQ_{16}Q_{16}$, —$S(O)_2NQ_{16}Q_{16}$, —$NQ_{16}S(O)_2Q_{16}$, —$NQ_{16}S(O)Q_{16}$, —$NQ_{16}SQ_{16}$, —$NO_2$, and —$SNQ_{16}Q_{16}$. The alkyl, cycloalkyl, and cycloalkenyl being further optionally substituted with =O or =S.

Each $Q_{16}$ is independently selected from —H, alkyl, and cycloalkyl. The alkyl and cycloalkyl optionally including 1-3 halos.

Other examples of oxazolidinone compounds and methods for producing oxazolidinone compounds may be found, for example, in the following publications which are hereby incorporated by reference in their entirety.

U.S. Pat. Nos. 5,225,565; 5,182,403; 5,164,510; 5,247,090; 5,231,188; 5,565,571; 5,547,950; 5,952,324; 5,968,962; 5,688,792; 6,069,160; 6,239,152; 5,792,765; 4,705,799; 5,043,443; 5,652,238; 5,827,857; 5,529,998; 5,684,

023; 5,627,181; 5,698,574; 6,166,056; 6,051,716; 6,043,266; 6,313,307; and 5,523,403.

PCT Application and publications PCT/US93/04850, WO94/01110; PCT/US94/08904, WO95/07271; PCT/US95/02972, WO95/25106; PCT/US95/10992, WO96/13502; PCT/US96/05202, WO96/35691; PCT/US96/12766; PCT/US96/13726; PCT/US96/14135; PCT/US96/17120; PCT/US96/19149; PCT/US97/01970; PCT/US95/12751, WO96/15130, PCT/US96/00718, WO96/23788, WO98/54161, WO99/29688, WO97/30995, WO97/09328, WO95/07271, WO00/21960, WO01/40236, WO99/64417, and WO01/81350.

In certain embodiments, the oxazolidinone can have the following formula:

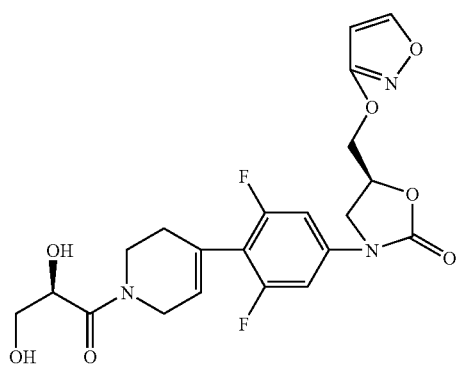

Oxazolidinones suitable for the invention typically are gram-positive antibacterial agents. Certain oxazolidinone compounds useful in the invention have been described in U.S. Pat. No. 5,688,792, the entire disclosure of which is incorporated herein by reference. Other suitable oxazolidinone compounds have the following Formula II:

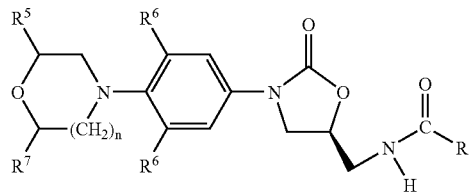

or is a pharmaceutically acceptable salt thereof, wherein:
n is 0, 1, or 2;
  R is selected from the group consisting of:
  hydrogen;
  $C_1$-$C_8$ alkyl optionally substituted with one or more substituents selected from the group consisting of F, Cl, hydroxy, $C_1$-$C_8$ alkoxy, $C_1$-$C_8$ acyloxy, or $CH_2$-phenyl;
  $C_3$-$C_6$ cycloalkyl;
  amino;
  $C_1$-$C_8$ alkylamino;
  $C_1$-$C_8$ dialkylamino; or
  $C_1$-$C_8$ alkoxy;
  $R^5$ at each occurrence is independently selected from the group consisting of H, $CH_3$, CN, $CO_2H$, $CO_2R$, and $(CH_2)_m R^{10}$, wherein m is 1 or 2;
  $R^6$ at each occurrence is independently selected from the group consisting of H, F, and Cl;
  $R^7$ is H, except when $R^1$ is $CH_3$, then $R^7$ is H or $CH_3$;

$R^{10}$ is selected from the group consisting of H, OH, OR, OCOR, $NH_2$, NHCOR, and $N(R^{11})_2$; and
  $R^{11}$ at each occurrence is independently selected from the group consisting of H, p-toluensulfonyl, and $C_1$-$C_4$ alkyl optionally substituted with one or more substituents selected from the group consisting of Cl, F, OH, $C_1$-$C_8$ alkoxy, amino, $C_1$-$C_8$ alkylamino, and $C_1$-$C_8$ dialkylamino.

As used herein, the term "pharmaceutically acceptable salts" refers to organic and inorganic acid addition salts of the parent compound. Examples of salts useful for the invention are, for example, hydrochloride, hydrobromide, hydroiodide, sulfate, phosphate, acetate, propionate, lactate, mesylate, maleate, malate, succinate, tartrate, citrate, 2-hydroxyethyl sulfate, fumarate, and the like.

One suitable oxazolidinone compound having the structure,

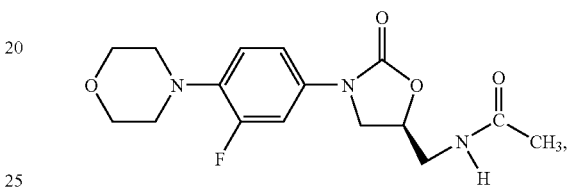

has the IUPAC name (S)-N-[[3-[3-fluoro-4-(4-morpholinyl)phenyl]-2-oxo-5-oxazolidinyl]methyl]acetamide. The compound is commonly known as linezolid and has demonstrated particularly effective anti-bacterial activity.

The linezolid compound can be prepared according any suitable method, including for example, general methods described in U.S. Pat. No. 5,688,792. Briefly, the heteroaryl substituent, for example an oxazine or thiazine moiety, is reacted with a functionalized nitrobenzene in the presence of a suitable base, preferably in an organic solvent, such as acetonitrile, tetrahydrofuran, or ethyl acetate. The nitro group is reduced either by hydrogenation or using a suitable reducing agent, for example aqueous sodium hydrosulfite, to afford an anilo compound. The anilo compound is converted into its benzyl or methyl urethane derivative, deprotonated with a lithium reagent to give a suitable lithiated intermediate, and treated with (−)-(R)-glycidyl butyrate to afford a crude oxazolidinone compound. A suitable method for preparing the linezolid compound is more particularly described in Example 5 of U.S. Pat. No. 5,688,792.

According to one embodiment of the invention, a method for preparing an infection-resistant medical device for use within a human or animal body includes the steps of providing a medical device and incorporating an effective amount of an antimicrobial agent comprising an oxazolidinone compound into the medical device.

The oxazolidinone compound can be a compound according to Formula I, as described above. The oxazolidinone compound can be linezolid, or a pharmaceutically acceptable salt thereof.

The medical device can be, for example, a suture, orthopedic appliance, stent, catheter, guidewire, shunt (e.g., hemodialysis shunt or cerebrospinal shunt), prosthesis (e.g., prosthetic heart valve or prosthetic joint), cardiac pacemaker, neuronal stimulator, or vascular graft. The medical device can be made of biomaterials (i.e., biologically-compatible materials known to those skilled in the art, such as metal, polymeric, or ceramic materials). The antimicrobial agent can be incorporated into the medical device according to methods known to those skilled in the art, such as by immersing the medical device in a solution (e.g., an aqueous solution) containing the antimicrobial agent, or, for example, by methods described in one of the following references: U.S. Pat. No. 3,987,797; U.S. Pat. No. 4,563,485; U.S. Pat. No. 4,875,479; U.S. Pat. No. 4,946,870; U.S. Pat. No. 5,306,289; U.S. Pat. No. 5,584,877; U.S. Pat. No. 5,607,685; U.S. Pat. No. 5,788,979; U.S. Pat. No. 6,143,037; U.S. Pat. No. 6,238,687; WO00/56283; and WO 01/28601, the disclosures of which are incorporated herein by reference. The medical device can include a polymeric material, and the polymeric material can be co-extruded with the antibacterial agent. The method for preparing an infection-resistant medical device can also include a step of heating the medical device to a temperature of about 100° C. to about 121° C. The method can include a step of heating the device in an autoclave, according to methods known to those skilled in the art (e.g., heating the device to a temperature of about 100° C. to about 121° C.; at a pressure of about 15 psi to about 20 psi; for a time period of about 15 min. to about 20 min.). Linezolid (an oxazolidinone), in contrast to other antibacterial compounds, has been discovered to be surprisingly resistant to thermal decomposition, at temperatures up to at least about 121° C.

The effective amount of the oxazolidinone compound is normally administered at a therapeutic dosage for treating antimicrobial infections in the range of about 0.1 to about 100, more preferably, about 3.0 to about 50 mg/kg of body weight/day. It is to be understood that the dosages may vary depending upon the requirements of the patient, the severity of the bacterial infection being treated, and the particular compound being used. These dosages can be administered to provide blood levels having between about 2 and about 4 times the minimum inhibitory concentration (MIC) of that antimicrobial agent. Of course, the MIC of a specific antimicrobial agent varies for each bacterial species. Advantageously, oxazolidinone compounds unexpectedly exhibit anti-adhesion properties at concentrations well below the MIC. As a result, oxazolidinone compounds inhibit bacterial adhesion after a single dosing for longer periods of time relative to other antimicrobial agents which exhibit anti-adhesion properties at concentrations equal to or greater than the MIC for those agents. The unexpected properties of the oxazolidinone compounds are particularly advantageous in inhibiting bacterial adhesion onto the surfaces of medical devices that are placed into the human or animal body in areas that experience lower antimicrobial agent concentration relative to other areas of the body, e.g., in areas of low or poor circulation, or higher variation of antimicrobial agent concentration after dosing. Due to the unexpected properties of the oxazolidinone compounds, the concentration of the oxazolidinone compound in the human or animal body, adjacent to the medical device, that remains effective as an anti-adhesion agent is less than the MIC. As described below in the Examples, linezolid has been discovered to be surprisingly effective at preventing bacterial adhesion onto surfaces of biologically-compatible materials at concentrations below the MIC, even at concentrations as low as one-fourth of the MIC. These materials, when implanted, may be effective at preventing bacterial adhesion at subinhibitory concentrations. Preventing bacterial adhesion assists in the effective treatment of bacterial infections, especially those that occur at or near the site of implanted medical devices, by disrupting typical bacteria pathogenesis, e.g., adherence of bacteria to biomaterials to form a multi-cell environment that protects the bacteria from anti-microbial agents and host defenses.

In general, the periodicity at which one administers regular dosages of an effective amount of a pharmaceutical composition containing one or more oxazolidinone compounds to inhibit bacterial adhesion should be adjusted to maintain the concentration of the pharmaceutical composition in the patient, adjacent to the implanted device, at or above about one-half of the MIC of the pharmaceutical composition or at or above one-fourth of the MIC of the pharmaceutical composition. Compositions including antibacterial agents that lack the unexpected sub-MIC anti-adhesion properties of the oxazolidinone compounds require higher effective amounts of the active agent and/or higher periodicity of dosing.

According to another embodiment, a method of inhibiting adherence of bacteria to a medical device includes the steps of providing an antibacterial agent comprising linezolid, or a pharmaceutically acceptable salt thereof, and incorporating the antibacterial agent into the medical device. The antibacterial agent can be incorporated into the medical device according to methods known to those skilled in the art, such as by immersing the medical device in a solution (e.g., an aqueous solution) containing the antimicrobial agent. The method of inhibiting adherence of bacteria to a medical device can include a step of heating the medical device to a temperature of about 100° C. to about 121° C. For instance, the device may be heated in an autoclave for sterilization prior to use, according to methods known to those skilled in the art (e.g., heating the device to a temperature of about 100° C. to about 121° C.; at a pressure of about 15 psi to about 20 psi; for a time period of about 15 min. to about 20 min.). The amount of the oxazolidinone compound in the human or animal body or adjacent to the medical device that is effective as an anti-adhesion agent can be less than the MIC.

According to still another embodiment, a method of inhibiting bacterial adherence to an implanted medical device includes the steps of implanting a medical device in a human or animal body, and applying an antibacterial agent comprising an oxazolidinone, or a pharmaceutically acceptable salt thereof, to the implanted medical device. (E.g., the antibacterial agent can be applied by placing a solution, paste, gel, or beads containing the antibacterial agent in contact with the device after the device is implanted.)

According to yet another embodiment, a method of inhibiting bacterial adherence to an implanted medical device includes the steps of administering a pharmaceutical composition comprising an oxazolidinone, or a pharmaceutically acceptable salt thereof, to a patient in need of an implanted medical device, and implanting a medical device in the patient. The pharmaceutical composition can be administered according to methods known to those skilled in the art, such as by oral administration or by intravenous administration. The composition can be administered before, during, and/or after surgery to implant the medical device. As described above, the effective amount of the oxazolidinone compound, such as linezolid, is administered at a normal therapeutic dosage for treating antimicrobial infections. Advantageously, oxazolidinone compounds unexpectedly exhibit anti-adhesion properties at concentrations well below the MIC. As a result, oxazolidinone compounds inhibit bacterial adhesion after a single dosing for longer periods of time relative to other antimicrobial agents which exhibit anti-adhesion properties at concentrations equal to or greater than the MIC.

According to a further embodiment, a medical device resistant to microbial adherence for use within a human or animal body includes linezolid, or a pharmaceutically acceptable salt thereof. The concentration of linezolid in the device is variable. Typically, the concentration of linezolid in the device is set at a level sufficient to generate a concentration of linezolid in the human or animal body, adjacent to the medical device, that is at least about one-half the MIC or at least about one-fourth the MIC.

To develop infection-resistant medical devices and methods, we compared the effects of linezolid and vancomycin on adherence of coagulase-positive and -negative *staphylococci* to polystyrene surfaces. Vancomycin, a glycopeptide that inhibits bacterial cell wall synthesis, was chosen as a comparator agent because it is frequently used as a prophylactic agent during implantation of prosthetic devices. A modified version of a microtiter-plate assay described by Christensen, et al., *J. Clin. Microbiol.* 22(6): 996-1006 (1985), was used as a direct measure of adherence. The basis of this assay is that bacterial cells adhere to polymeric material and to each other, forming a macrocolony whose density is measured spectrophotometrically after staining with crystal violet. The reliability of this assay was assessed with adherent and nonadherent staphylococci reference strains and verified by image analysis using scanning electron microscopy.

The importance of plastic adherence as a surrogate marker for virulence has been supported by several clinical studies. (See Davenport, et al. *J. Infect. Dis.* 153(2): 332-339 (1986); Deighton, et al., *J. Clin. Microbiol.* 28(11): 2442-2447 (1990).)Staphylococci strains that adhere to and grow on biomaterials were more often associated with significant infections than nonadherent strains.

Many different techniques have been employed to study the effects of antimicrobial agents on bacterial adherence, biofilm formation, and cell-cell communication. Methods can be divided broadly into two groups, static and dynamic. The adherence assay described herein is a static model using polystyrene as the substratum. (A dynamic approach uses laminar flow of a bacterial suspension through a perfusion chamber with channels containing engineered materials.) In this static model, scanning electron micrographs of the reference strain RP62A displayed multicell macrocolonies with pillar-like structures separated by water-filled spaces. See FIGS. 7A-D. These findings are indicative of a biofilm presence. Static models allow rapid testing of several clinical isolates against a panel of antimicrobial agents.

In this model, linezolid was shown to be surprisingly effective in preventing staphylococcal adherence and colonization at subtherapeutic levels (i.e., concentrations of less than the minimum inhibitory concentration (MIC)). The Examples below illustrate that linezolid, at concentrations less than the MIC, and as low as one-fourth the MIC, exerts significant inhibitory effects on cell adhesion in all strains evaluated. In contrast, subtherapeutic levels of vancomycin did not inhibit staphylococcal adherence in four of the five strains assessed.

In contrast to the effectiveness of linezolid, other investigators also have shown that subinhibitory concentrations of vancomycin have minimal or no activity against bacterial adherence. (See Carsenti-Etesse, et al., *Antimicrob. Agents Chemother.* 37(4): 921-923 (1993); Rupp, et al., *J. Antimicrob. Chemother.* 41:155-161 (1998); Schadow, et al., *J. Infect. Dis.* 157(1): 71-77 (1988); Wilcox et al., *J. Antimicrob. Chemother.* 27:577-587 (1991).)

In another aspect, oxazolidinones, such as linezolid, unexpectedly exhibit long-term efficacy at inhibiting adhesion of coagulase-negative staphylococci to polystyrene surfaces at sub-MIC levels.

The following examples demonstrate illustrative embodiments of the invention:

EXAMPLES

Example 1

Bacterial Isolates

Staphylococci isolates were obtained from the blood of patients with catheter-related sepsis. Isolates were speciated using the API STAPH identification system (bioMerieux, Marcy-l'Etoile, France) and were selected on the basis of their adherence properties. The reference strains *S. epidermidis* RP62A and *S. hominis* SP-2 were obtained from the American Type Culture Collection (Manassas, Va.). RP62A produces polysaccharide adhesins and demonstrates strong adherence to surfaces of synthetic polymers. SP-2 is a nonadherent strain and was used as a negative control for the adherence assay. Working stock cultures (1 ml aliquots) were frozen in trypticase soy broth (TSB) with 20% glycerol and kept in the vapor phase of liquid nitrogen. Before each experiment, one aliquot was thawed and subcultured on blood agar plates at 37° C. for 24 hours.

Example 2

Antimicrobial Agents

Linezolid (Pharmacia Corp., Kalamazoo, Mich.) and vancomycin (Sigma Chemical Co., St. Louis, Mo.) were used in this study.

Linezolid and vancomycin were dissolved in 20% dimethylsulfoxide/water, sterilized by filtration through a 0.22 µm membrane filter (PALL Gelman Laboratory, Ann Arbor, Mich.), and diluted in TSB to the appropriate working concentrations. The final concentration of DMSO was less than 0.1% in all test wells.

Example 3

Determination of Minimum Inhibitory Concentrations

A minimum inhibitory concentration (MIC) value for each clinical isolate was determined by the microdilution method (NCCLS 2000) using the conditions under which adherence was measured. The MIC was defined as the lowest concentration of linezolid or vancomycin that inhibited >99.0% of bacterial growth when compared to drug-free cultures (growth controls). Growth inhibition was assessed by optical density readings of culture turbidity after 18 h of incubation with drug. Since visual interpretation of MIC endpoints may be subjective, the spectrophotometric measurements of culture turbidity allowed standardized assessment of MIC values across and within drug treatments. The MIC value was noted for each strain, as well as the values for one-half (½ MIC), and one-fourth (¼ MIC) of the MIC. Antimicrobial agents at concentrations equal to the MIC eliminate the virulence of any given organism because these concentrations inhibit or kill the offending organism. Concentrations below the dose that prevents growth or kills the organism must be used to study the effects of antimicrobial agents on virulence factors, such as cell adherence.

Example 4

Adherence Assay

The effects of linezolid and vancomycin on adherence of staphylococci to polystyrene were measured by using an established microtiter-plate assay first described by Christensen et al. (Christensen, et al., J. Clin. Microbiol. 22(6): 996-1006 (1985).) Minor modifications to the procedure were made. Briefly, the inoculum was established by the direct colony suspension method using the Prompt™ Inoculation System (Becton Dickinson, Sparks, Md.). The bacteria suspension, which was equal to the turbidity of a 0.5 McFarland standard, was diluted in TSB to a concentration of $1 \times 10^6$ colony forming units per ml (CFU/mL). One hundred microliters of the cell suspension was added to flat-bottom polystyrene wells (Corning Costar, Corning, N.Y.) containing 100 µl of TSB, with and without drug. The final inoculum concentration per well was approximately $5 \times 10^5$ CFU/mL. The plates were incubated at 37° C. under static conditions in air. At 18 hours (h) post-infection, the optical density of bacterial growth was measured at a wavelength of 595 nm in a microtiter plate reader (Vmax; Molecular Devices, Sunnyvale, Calif.). For quantitative assessment of adherent bacteria, the medium was aspirated carefully and each well was washed three times with phosphate-buffered saline to remove free-floating "planktonic" cells. Adherent "sessile" cells then were fixed with 3.7% (v/v) formaldehyde/2% (w/v) sodium acetate and stained with 0.1% (w/v) crystal violet. Excess stain was rinsed off with deionized water and the plates were air-dried for 4 h. The optical density of bacterial adherence was determined at a wavelength of 550 nm. Preliminary studies were performed to determine the optimal wavelengths for measuring growth turbidity and stained adherent cells (data not shown). To compensate for background absorbance, optical density readings from wells treated with sterile medium, fixative and stain as described above were averaged and then subtracted from all test and control wells. Relative inhibition of adherence or growth was expressed by the following equation: (OD of control well–OD of treated well/OD of control well)×100, where OD is the mean optical density of six replicate wells from two separate experiments (three replicates per experiment). Control was defined as infected, drug-free cultures.

Example 5

Statistical Methods

The primary efficacy variable in this study was the measurement of adherent bacterial cells to polystyrene after 18 h of growth. To determine whether statistically significant differences existed between treatment groups (MIC, ½ MIC, and ¼ MIC) compared with the infected-nontreated controls, the Kruskal-Wallis one-way analysis of variance (ANOVA) was applied for each clinical strain. Statistical significance was defined as p-values $\leq 0.05$. An asterisk (*) was placed by all test values less than or equal to the specified significance level.

Example 6

Scanning Electron Microscopy

A semiquantitative assessment of adherent organisms to the surface of polystyrene was ascertained by scanning electron microscopy (SEM). Bacterial cultures of S. aureus UC-20205 and S. epidermidis RP62A were set up in Lab-Tek® chamber slides (Nalge Nunc International, Naperville, Ill.) under the same conditions used in the adherence assay. The medium was aspirated and each chamber was washed three times with phosphate-buffered saline to remove planktonic cells. Sessile cells that adhered to the polymer surface as well as to each other were fixed for two hours in 3% glutaraldehyde in 0.1 M phosphate buffer (pH 7.3). Osmium tetroxide solution (1%) was used as a second fixative. Specimens were dehydrated in a series of aqueous ethanol solutions (30%-100%) followed by critical point drying with hexamethydisilazane. The slides were allowed to dry overnight and then were coated with gold by using a Polaron E5200 SEM autocoating unit (Polaron Instruments). Microcolonies were examined by using an ISI DS 130 scanning electron microscope.

Example 7

Minimum Inhibitory Concentration (MIC) Values

MIC data for the six clinical isolates are summarized in Table 1, below:

TABLE 1

In Vitro Activity of Linezolid and Vancomycin Against Staphylococcal Isolates Recovered from Patients with Intravascular Catheter-associated Sepsis

| | | MIC†(µg/ml) | |
|---|---|---|---|
| Species | Strain | Linezolid | Vancomycin |
| S. aureus | UC-20205 | 2 | 1 |
| | UC-20206 | 4 | 1 |
| S. epidermidis | UC-20207 | 2 | 2 |
| | UC-20208 | 2 | 2 |
| | RP62A | 2 | 2 |
| S. hominis | SP-2 | 2 | 1 |

†minimum inhibitory concentration

Both linezolid and vancomycin demonstrated potent activity against all the organisms tested. MIC values were similar between the two antibacterial agents, with the exception of one strain (S. aureus UC-20206) that showed a slightly higher value for linezolid (4 µg/ml) compared to vancomycin (1 µg/ml).

Example 8

Effects of Subinhibitory Concentrations on Adherence

Experimental results for the effects of subinhibitory concentrations of linezolid on the adherence of S. aureus and S. epidermidis strains are presented in Table 2 below:

TABLE 2

Inhibitory Effects of Therapeutic and Subtherapeutic Treatments with Linezolid on Bacterial Adherence of Clinical Isolates That Have the Potential to Colonize Abiotic Surfaces

| | | Drug | Adherence | |
|---|---|---|---|---|
| Species | Strain | µg/ml | Mean OD$_{550}$‡ | % Inhibition |
| S. aureus | UC-20205 | 2.0† | 0.001 ± 0.001* | 99.7 |
| | | 1.0 | 0.005 ± 0.007* | 99.0 |

TABLE 2-continued

Inhibitory Effects of Therapeutic and Subtherapeutic Treatments with Linezolid on Bacterial Adherence of Clinical Isolates That Have the Potential to Colonize Abiotic Surfaces

| Species | Strain | Drug µg/ml | Adherence Mean OD$_{550}$‡ | % Inhibition |
|---|---|---|---|---|
| | | 0.5 | 0.013 ± 0.007* | 97.6 |
| | | control | 0.531 ± 0.107 | — |
| | UC-20206 | 4.0† | 0.003 ± 0.003* | 98.5 |
| | | 2.0 | 0.002 ± 0.002* | 99.3 |
| | | 1.0 | 0.001 ± 0.002* | 99.4 |
| | | control | 0.224 ± 0.027 | — |
| S. epidermidis | UC-20207 | 2.0† | 0.010 ± 0.005* | 99.5 |
| | | 1.0 | 0.007 ± 0.002* | 99.7 |
| | | 0.5 | 0.513 ± 0.227* | 76.9 |
| | | control | 2.220 ± 0.310 | — |
| | UC-20208 | 2.0† | 0.000 ± 0.001* | 100.0 |
| | | 1.0 | 0.001 ± 0.002* | 99.9 |
| | | 0.5 | 1.342 ± 0.791 | 26.7 |
| | | control | 1.831 ± 0.208 | — |
| | RP62A | 2.0† | 0.001 ± 0.001* | 100.0 |
| | | 1.0 | 0.002 ± 0.002* | 99.9 |
| | | 0.5 | 0.125 ± 0.133* | 95.5 |
| | | control | 2.805 ± 0.294 | — |

*Significantly different from infected-nontreated control cultures (P ≤ 0.05)
†Minimum inhibitory concentration
‡Values are mean optical density readings of six replicate wells from two separate experiments (three replicates per experiment) ± standard deviation Experimental results for the effects of subinhibitory concentrations of vancomycin on the adherence of S. aureus and S. epidermidis strains are presented in Table 3 below:

TABLE 3

Inhibitory Effects of Therapeutic and Subtherapeutic Treatments with Vancomycin on Bacterial Adherence of Clinical Isolates That Have the Potential to Colonize Abiotic Surfaces

| Species | Strain | Drug µg/ml | Adherence Mean OD$_{550}$‡ | % Inhibition |
|---|---|---|---|---|
| S. aureus | UC-20205 | 1.0† | 0.000 ± 0.001* | 100.0 |
| | | 0.5 | 0.012 ± 0.013* | 98.0 |
| | | 0.25 | 0.730 ± 0.202 | 0.0 |
| | | control | 0.584 ± 0.098 | — |
| | UC-20206 | 1.0† | 0.000 ± 0.003* | 9.99 |
| | | 0.5 | 0.267 ± 0.044 | 0.0 |
| | | 0.25 | 0.192 ± 0.020 | 12.5 |
| | | control | 0.219 ± 0.026 | — |
| S. epidermidis | UC-20207 | 2.0† | 0.001 ± 0.002* | 100.0 |
| | | 1.0 | 2.799 ± 0.120 | 0.0 |
| | | 0.5 | 2.177 ± 0.424 | 0.0 |
| | | control | 2.129 ± 0.406 | — |
| | UC-20208 | 2.0† | 0.000 ± 0.001* | 100.0 |
| | | 1.0 | 2.716 ± 0.400 | 0.0 |
| | | 0.5 | 2.165 ± 0.150 | 0.0 |
| | | control | 1.844 ± 0.138 | — |
| | RP62A | 2.0† | 0.000 ± 0.002* | 100.0 |
| | | 1.0 | 1.728 ± 0.952 | 36.6 |
| | | 0.5 | 2.816 ± 0.377 | 0.0 |
| | | control | 2.727 ± 0.257 | — |

*Significantly different from infected-nontreated control cultures (P < 0.05)
†Minimum inhibitory concentration
‡Values are mean optical density readings of six replicate wells from two separate experiments (three replicates per experiment) ± standard deviation The experimental results presented in Tables 2 and 3 above, showing the effects of subinhibitory concentrations of linezolid and vancomycin on the adherence of S. aureus and S. epidermidis strains, are summarized and presented graphically in FIGS. 1 through 5. Specifically, FIGS. 1-5 are graphs illustrating the effects of subinhibitory concentrations of linezolid and vancomycin on the adherence of the following strains of S. aureus and S. epidermidis to polystyrene: (FIG. 1) S. aureus UC-20205; (FIG. 2) S. aureus UC-20206; (FIG. 3) S. epidermidis UC-20207; (FIG. 4) S. epidermidis UC-20208; and (FIG. 5) S. epidermidis RP62A.

As shown in Table 2 and FIGS. 1-5, linezolid was highly effective in suppressing bacterial adherence to polystyrene surfaces at one-half the MIC. The percent inhibition of adherence relative to control was greater than or equal to 99.0% in all strains evaluated. Adherence optical density readings from linezolid treated cultures were significantly (p≦0.05) decreased when compared to infected-nontreated cultures. Linezolid was also effective in preventing adherence at one-fourth the MIC in all but one strain (S. epidermidis UC-20208). A statistical difference in optical density readings for treated versus nontreated cultures was also noted in 4 of the 5 strains assessed. In contrast, as shown in Table 3 and FIGS. 1-5, subinhibitory concentrations of vancomycin showed minimal or no activity against bacterial adhesion, with the exception of one strain (S. aureus UC-20205) that was exposed to one-half the MIC.

Reliability of the microtiter-plate adherence assay was assessed with the reference strains S. hominis SP2 (nonadherent) and S. epidermidis RP62A (strongly adherent). The median optical density readings for SP2 and RP62A were 0.059±0.004 and 2.789±0.266, respectively. Values ranged from 0.055 to 0.067 for SP2 and from 2.466 to 3.234 for RP62A. The data reported herein represent 12 replicate wells per strain. These results were similar to those documented in published reports (see Deighton, et al., J. Clin. Microbiol. 28(11): 2442-2447 (1990)), and indicate that the microtiter-plate assay for determining adherence is reliable and reproducible. Neither linezolid nor vancomycin promoted adherence of the nonadherent strain, SP2 (data not shown).

Scanning electron micrographs of S. aureus UC-20205 and S. epidermidis RP62A exposed to linezolid and vancomycin at one-fourth the MIC are illustrated in FIGS. 6 and 7. Specifically, FIGS. 6A-D are scanning electron micrographs showing microcolonies of S. aureus UC-20205 adherent to a polystyrene surface: (A) noninfected control; (B) infected-nontreated control; (C) infected culture treated with linezolid at one-fourth the MIC; and (D) infected culture treated with vancomycin at one-fourth the MIC. FIGS. 7A-D are scanning electron micrographs showing microcolonies of S. epidermidis RP62A adherent to a polystyrene surface: (A) noninfected control; (B) infected-nontreated control; (C) infected culture treated with linezolid at one-fourth the MIC; and (D) infected culture treated with vancomycin at one-fourth the MIC. In infected-nontreated cultures, adhesin proteins were observed on the cell surface of strain UC-20205, whereas RP62A displayed multiple layers of sessile cells that adhered to the polymer surface as well as to each other. Cell aggregation in multicell layers, "sessile communities," is indicative of biofilm formation. Unfortunately, the fixatives and dehydrating agents used to process the specimens dissolved this extracellular matrix, leaving a scaffolding appearance. These micrographs of cultures that were treated prophylactically with subinhibitory concentrations of linezolid or vancomycin support the findings from the microtiter-plate assay. The number of adherent bacteria that were observed on the polystyrene surface were substantially reduced in linezolid treated cultures when compared to nontreated cultures. Only a few isolated microcolonies were seen. No effects on bacterial adherence were noted in the vancomycin treated cultures for both staphylococci strains examined.

Example 9

Inhibitory Effects of Linezolid on Staphylococcal Adherence Versus Time of Treatment Anti-adhesion effects of linezolid and vancomycin on three *S. epidermidis* isolates (UC-20207, UC-20208, and RP62A) recovered from patients with catheter-related bloodstream infections were studied.

As illustrated in Table 4 below, bacterial suspensions ($5 \times 10^5$ CFU/mL) were added to polystyrene wells and treated with one-half to four times the MIC of linezolid or vancomycin at 0, 2, 4, or 6 hours post-inoculation. Drug effects on bacterial adherence were measured 18 hours after treatment initiation using a quantitative spectrophotometric assay.

Relative inhibition of adherence was expressed by the following equation: (OD of control well–OD of treated well/OD of control well)×100, where OD is the mean optical density of six replicate wells from two separate experiments (three replicates per experiment). Control was defined as infected, drug-free cultures.

The primary efficacy variable in this study was the measurement of adherent bacteria to polystyrene surfaces after 18 hours to 24 hours of growth. To determine whether statistically significant differences existed between treatments (4×MIC, 2×MIC, MIC, and ½ MIC) compared with the infected-nontreated controls, multiple comparisons according to Dunnett's test (Montgomery, *Design and Analysis of Experiments* (1991)) were applied for each clinical strain. Differences were considered statistically significant when $p<0.05$.

Experimental results for inhibitory effects of therapeutic ($\geq$MIC) and subtherapeutic (one-half MIC) treatments of linezolid on *S. epidermidis* strains for various time intervals prior to treatment, are presented in Table 5 below. Values having a statistically significant difference, compared to control, are indicated by an asterisk (*).

TABLE 4

Time Course Adherence Assay

| Treatment Group | Time between inoculation and treatment with linezolid or vancomycin (hours) | Time between treatment with linezolid or vancomycin and spectrophotometric assay (hours) | Time between inoculation and spectrophotometric assay (hours) |
|---|---|---|---|
| 1 | 0 | 18 | 18 |
| 2 | 2 | 18 | 20 |
| 3 | 18 | 22 | |
| 4 | 6 | 18 | 24 |

TABLE 5

Inhibitory Effects of Therapeutic and Subtherapeutic Treatments of Linezolid on *S. epidermidis* Strains for Various Time Intervals Prior to Treatment

| | | Delayed Treatment with Drug Regimen | | | | | | | |
|---|---|---|---|---|---|---|---|---|---|
| | Linezolid | 0 h† | | 2 h† | | 4 h† | | 6 h† | |
| Strain | µg/ml | Mean OD$_{550}$‡ | % § | Mean OD$_{550}$‡ | % § | Mean OD$_{550}$‡ | % § | Mean OD$_{550}$‡ | % § |
| UC-20207 | 80 | 0.005 ± 0.002* | 99.8 | 0.009 ± 0.003* | 99.6 | 0.028 ± 0.020* | 99.0 | 0.662 ± 0.103* | 75.1 |
| | 4.0 | 0.009 ± 0.004* | 99.6 | 0.007 ± 0.001* | 99.7 | 0.022 ± 0.010* | 99.2 | 1.558 ± 0.094* | 41.4 |
| | 2.0¶ | 0.024 ± 0.005* | 99.0 | 0.004 ± 0.002* | 99.8 | 0.356 ± 0.418* | 87.8 | 2.938 ± 0.119 | 0.0 |
| | 1.0 | 0.084 ± 0.049* | 96.5 | 0.064 ± 0.046* | 97.5 | 0.921 ± 0.119 | 68.4 | 2.757 ± 0.173 | 0.0 |
| | control | 2.391 ± 0.214 | — | 2.530 ± 0.228 | — | 2.913 ± 0.285 | — | 2.658 ± 0.181 | — |
| UC-20208 | 8.0 | 0.000 ± 0.001* | 100.0 | 0.004 ± 0.001* | 99.7 | 0.000 ± 0.003* | 100.0 | 0.092 ± 0.053* | 89.1 |
| | 4.0 | 0.002 ± 0.001* | 99.8 | 0.004 ± 0.001* | 99.7 | 0.000 ± 0.001* | 100.0 | 0.363 ± 0.280* | 56.8 |
| | 2.0¶ | 0.001 ± 0.001* | 99.9 | 0.003 ± 0.000* | 99.8 | 0.000 ± 0.003* | 100.0 | 1.602 ± 0.300 | 0.0 |
| | 1.0 | 0.001 ± 0.002* | 99.9 | 0.003 ± 0.001* | 99.8 | 0.856 ± 0.472 | 22.1 | 1.127 ± 0.133 | 0.0 |
| | control | 1.161 ± 0.224 | — | 1.434 ± 0.108 | — | 1.099 ± 0.170 | — | 0.842 ± 0.259 | — |
| RP62A | 8.0 | 0.002 ± 0.002* | 99.9 | 0.003 ± 0.001* | 99.8 | 0.000 ± 0.001* | 100.0 | 0.021 ± 0.010* | 98.4 |
| | 4.0 | 0.002 ± 0.002* | 99.9 | 0.003 ± 0.002* | 99.9 | 0.002 ± 0.004* | 99.8 | 0.082 ± 0.051* | 93.5 |
| | 2.0¶ | 0.004 ± 0.004* | 99.8 | 0.001 ± 0.001* | 99.9 | 0.003 ± 0.005* | 99.8 | 0.083 ± 0.067* | 93.4 |
| | 1.0 | 0.000 ± 0.002* | 100.0 | 0.000 ± 0.000* | 100.0 | 0.000 ± 0.001* | 100.0 | 0.274 ± 0.183* | 78.4 |
| | control | 2.234 ± 0.223 | — | 1.915 ± 0.272 | — | 1.268 ± 0.179 | — | 1.266 ± 0.593 | — |

*Significantly different from infected-nontreated control cultures ($p < 0.05$);
†Time post-infection (hours);
‡Values are mean optical density readings of six replicate wells from two separate experiments (three replicates per experiment) ±standard deviation;
§Percent inhibition of bacterial adherence relative to controls ([OD of control well – OD of treated well/OD of control well] × 100);
¶Minimum inhibitory concentration (MIC)

Experimental results for inhibitory effects of therapeutic (≧MIC) and subtherapeutic (one-half MIC) treatments of vancomycin on *S. epidermidis* strains for various time intervals prior to treatment, are presented in Table 6 below. Values having a statistically significant difference, compared to control, are indicated by an asterisk (*).

TABLE 6

Inhibitory Effects of Therapeutic and Subtherapeutic Treatments of Vancomycin on *S. epidermidis* Strains for Various Time Intervals Prior to Treatment

| Strain | Vancomycin μg/ml | Delayed Treatment with Drug Regimen | | | | | | | |
|---|---|---|---|---|---|---|---|---|---|
| | | 0 h† | | 2 h† | | 4 h† | | 6 h† | |
| | | Mean $OD_{550}$ ‡ | % § | Mean $OD_{550}$ ‡ | % § | Mean $OD_{550}$‡ | % § | Mean $OD_{550}$ ‡ | % § |
| UC-20207 | 8.0 | 0.003 ± 0.002* | 99.9 | 0.007 ± 0.003* | 99.7 | 0.028 ± 0.014* | 99.0 | 0.326 ± 0.046* | 88.5 |
| | 4.0 | 0.003 ± 0.002* | 99.9 | 0.006 ± 0.003* | 99.8 | 0.033 ± 0.010* | 98.8 | 3.050 ± 0.343 | 0.0 |
| | 2.0¶ | 0.005 ± 0.004* | 99.8 | 0.014 ± 0.010* | 99.4 | 2.693 ± 0.527 | 3.6 | 2.979 ± 0.168 | 0.0 |
| | 1.0 | 2.389 ± 0.175 | 0.0 | 2.723 ± 0.294 | 0.0 | 2.824 ± 0.153 | 0.0 | 2.959 ± 0.245 | 0.0 |
| | control | 2.297 ± 0.180 | — | 2.542 ± 0.169 | — | 2.794 ± 0.224 | — | 2.839 ± 0.140 | — |
| UC-20208 | 8.0 | 0.001 ± 0.001* | 99.9 | 0.000 ± 0.001* | 100.0 | 0.006 ± 0.002* | 99.6 | 3.099 ± 0.351 | 0.0 |
| | 4.0 | 0.001 ± 0.001* | 99.9 | 0.000 ± 0.001* | 100.0 | 0.239 ± 0.261* | 85.1 | 1.555 ± 0.206 | 0.0 |
| | 2.0¶ | 0.001 ± 0.000* | 99.9 | 0.014 ± 0.036* | 99.1 | 2.414 ± 0.558 | 0.0 | 1.281 ± 0.555 | 0.0 |
| | 1.0 | 1.865 ± 0.309 | 0.0 | 1.865 ± 0.435 | 0.0 | 1.752 ± 0.566 | 0.0 | 1.127 ± 0.463 | 0.0 |
| | control | 1.171 ± 0.139 | — | 1.509 ± 0.155 | — | 1.606 ± 0.252 | — | 0.890 ± 0.374 | — |
| RP62A | 8.0 | 0.001 ± 0.001* | 99.9 | 0.000 ± 0.001* | 100.0 | 0.004 ± 0.004* | 99.8 | 0.025 ± 0.030* | 98.7 |
| | 4.0 | 0.002 ± 0.002* | 99.9 | 0.000 ± 0.002* | 100.0 | 0.003 ± 0.004* | 99.8 | 1.562 ± 0.573 | 19.0 |
| | 2.0¶ | 0.002 ± 0.002* | 99.9 | 0.000 ± 0.001* | 100.0 | 1.312 ± 0.936 | 29.4 | 2.114 ± 0.439 | 0.0 |
| | 1.0 | 0.664 ± 0.632* | 69.3 | 1.147 ± 0.527 | 41.4 | 2.311 ± 0.318 | 0.0 | 2.202 ± 0.238 | 0.0 |
| | control | 2.159 ± 0.278 | — | 1.958 ± 0.310 | — | 1.858 ± 0.261 | — | 1.928 ± 0.266 | — |

*Significantly different from infected-nontreated control cultures ($p < 0.05$);
†Time post-infection (hours);
‡Values are mean optical density readings of six replicate wells from two separate experiments (three replicates per experiment) ±standard deviation;
§Percent inhibition of bacterial adherence relative to controls ([OD of control well − OD of treated well/OD of control well] × 100);
¶Minimum inhibitory concentration (MIC)

Therapeutic levels (≧MIC) of linezolid demonstrated potent anti-adhesion activity following 2- and 4-hour deferred treatments. See Table 5, FIGS. 8 and 9. The percent inhibition of adherence relative to controls ranged from 87.8% to 100%. Even at subtherapeutic concentrations (one-half MIC), suppression of staphylococcal adherence was still evident in most cultures; mean inhibitory effects were 99.1%±1.4 (2 h) and 63.5%±39.2 (4 h). See FIG. 10. Linezolid at 4×MIC also exerted significant inhibitory effects (87.5%±11.7) in cultures that had been treated with a 6-hour delay. Therapeutic levels of vancomycin administered 2 hours post-infection were equally effective. However, subtherapeutic concentrations showed minimal or no activity against cell adhesion. See Table 6, FIGS. 8, 9, and 11. When vancomycin treatments were delayed by 4 to 6 hours, only the highest concentrations (>MIC) demonstrated anti-adhesion activity.

The results demonstrate that oxazolidinones such as linezolid have important implications for antimicrobial prophylaxis in patients with implanted medical devices.

The foregoing detailed description is given for clearness of understanding only, and no unnecessary limitations should be understood therefrom, as modifications within the scope of the invention may become apparent to those skilled in the art.

We claim:

1. A method of preparing a medical device resistant to microbial adherence said method comprising a step of incorporation of an effective amount of linezolid into the medical device wherein the step of incorporation comprises immersing the medical device in an aqueous solution of linezolid wherein the concentration of linezolid is about one-fourth the MIC of *S. aureus* UC-20205 or greater.

2. The method of claim 1, further comprising a step of heating the medical device, after the step of incorporation, to a temperature of about 100° C. to about 121° C.

3. The method of claim 1 wherein the medical device comprises a polymeric material and the step of incorporation comprises co-extruding the polymeric material of an medical device with linezolid.

4. The method of claim 1 wherein the microbial adherence is caused by *staphylococci* organisms.

5. The method of claim 3 wherein the *staphylococci* organisms are selected from the group consisting of *S. aureus*, *S. epidermidis*; and *S. hominis*.

6. The method of claim 1 wherein the medical device is a suture, orthopedic appliance, stent, catheter, guidewire, shunt, prosthesis, cardiac pacemaker, neuronal stimulator, or vascular graft.

7. The method of claim 1 wherein the effective amount of linezolid is less than the minimum inhibitory concentration of the linezolid or the effective amount results in a concentration of the linezolid in the human or animal body, adjacent to the medical device, that is less than the minimum inhibitory concentration of the linezolid.

8. The method of claim 1 wherein the effective amount of linezolid is about one-fourth the MIC for *S. aureus* UC-20205 or the effective amount results in a concentration of the linezolid in the human or animal body, adjacent to the medical device, that is about one-fourth the MIC for *S. aureus* UC-20205.

9. The method of claim 1 wherein the effective amount of linezolid is about one-half the MIC for *S. aureus* UC-20205 or the effective amount results in a concentration of the linezolid in the human or animal body, adjacent to the medical device, that is about one-half the MIC for *S. aureus* UC-20205.

10. The method of claim 1 wherein the effective amount of linezolid is about one-fourth or one-half the MIC for *S. aureus* UC-20205 or the effective amount results in a concentration of the linezolid in the human or animal body, adjacent to the medical device, that is about one-fourth or one-half the MIC for *S. aureus* UC-20205.

* * * * *